United States Patent
Matsuda

(10) Patent No.: US 10,807,123 B2
(45) Date of Patent: Oct. 20, 2020

(54) ULTRASONIC TRANSDUCER HAVING AT LEAST TWO PAIRS OF ELECTRODES SANDWICHING A PIEZOELECTRIC BODY

(71) Applicant: SEIKO EPSON CORPORATION, Tokyo (JP)

(72) Inventor: Hiroshi Matsuda, Gifu (JP)

(73) Assignee: Seiko Epson Corporation (JP)

( * ) Notice: Subject to any disclaimer, the term of this patent is extended or adjusted under 35 U.S.C. 154(b) by 114 days.

(21) Appl. No.: 16/091,376

(22) PCT Filed: Mar. 30, 2017

(86) PCT No.: PCT/JP2017/013299
§ 371 (c)(1),
(2) Date: Oct. 4, 2018

(87) PCT Pub. No.: WO2017/175660
PCT Pub. Date: Oct. 12, 2017

(65) Prior Publication Data
US 2019/0151898 A1 May 23, 2019

(30) Foreign Application Priority Data
Apr. 6, 2016 (JP) .................................. 2016-076475

(51) Int. Cl.
*B06B 1/06* (2006.01)
*H04R 3/00* (2006.01)
(Continued)

(52) U.S. Cl.
CPC .............. *B06B 1/0666* (2013.01); *A61B 8/44* (2013.01); *A61B 8/4483* (2013.01);
(Continued)

(58) Field of Classification Search
CPC ........................ B06B 1/06–0696; H01L 41/00
See application file for complete search history.

(56) References Cited

U.S. PATENT DOCUMENTS 4,376,302 A * 3/1983 Miller ................... B06B 1/0696
310/358
4,583,018 A * 4/1986 Izumi .................... B06B 1/0644
310/334
(Continued)

FOREIGN PATENT DOCUMENTS

JP  H07-136164 A  5/1995
JP  H07-194517 A  8/1995
(Continued)

*Primary Examiner* — Tran M. Tran
(74) *Attorney, Agent, or Firm* — Harness, Dickey & Pierce, P.L.C.

(57) ABSTRACT

An ultrasonic transducer includes: a flexible film; and a piezoelectric element provided on the flexible film. The piezoelectric element includes a piezoelectric body and a first electrode, a second electrode, a third electrode, and a fourth electrode in contact with the piezoelectric body. The first electrode and the second electrode are separated from each other with the piezoelectric body interposed between the first electrode and the second electrode and overlapping each other in plan view. The third electrode and the fourth electrode are separated from each other with the piezoelectric body interposed between the third electrode and the fourth electrode and overlapping each other in the plan view. The first electrode and the third electrode are separated from each other in the plan view, and the second electrode and the fourth electrode are separated from each other in the plan view.

7 Claims, 13 Drawing Sheets

(51) Int. Cl.
*H01L 41/047* (2006.01)
*H01L 41/09* (2006.01)
*H01L 41/113* (2006.01)
*H04R 17/00* (2006.01)
*A61B 8/00* (2006.01)
*B06B 1/02* (2006.01)
*G01N 29/24* (2006.01)

(52) U.S. Cl.
CPC ......... *A61B 8/4488* (2013.01); *A61B 8/4494* (2013.01); *B06B 1/0207* (2013.01); *B06B 1/0622* (2013.01); *G01N 29/2437* (2013.01); *H01L 41/047* (2013.01); *H01L 41/09* (2013.01); *H01L 41/113* (2013.01); *H04R 3/00* (2013.01); *H04R 17/00* (2013.01); *A61B 8/54* (2013.01); *B06B 2201/76* (2013.01)

(56) References Cited

U.S. PATENT DOCUMENTS

| | | | | |
|---|---|---|---|---|
| 6,342,753 B1* | 1/2002 | Oliver | ................ | H01L 41/107 310/359 |
| 6,469,421 B1* | 10/2002 | Wakabayashi | ...... | H01L 41/0805 310/328 |
| 6,515,402 B2 | 2/2003 | Klee et al. | | |
| 6,906,451 B2* | 6/2005 | Yamada | ................ | C23C 14/10 310/324 |
| 7,240,410 B2* | 7/2007 | Yamada | ................ | C23C 14/10 29/25.35 |
| 7,446,455 B2* | 11/2008 | Iwasaki | ............... | H03H 9/0095 310/321 |
| 7,522,388 B2* | 4/2009 | Miyazawa | ............ | B82Y 25/00 360/324 |
| 7,667,558 B2* | 2/2010 | Nakatsuka | .......... | H03H 9/0095 310/366 |
| 8,148,881 B2* | 4/2012 | Yoneyama | ........... | B06B 1/0696 310/328 |
| 8,193,685 B2* | 6/2012 | Klee | ................... | B06B 1/0292 310/344 |
| 8,771,192 B2* | 7/2014 | Kano | .................. | G10K 11/004 600/459 |
| 8,820,165 B2* | 9/2014 | Matsuda | ............... | G01N 29/24 73/627 |
| 8,866,366 B2* | 10/2014 | Nakazawa | ............. | H01L 27/20 310/318 |
| 9,082,394 B2* | 7/2015 | Matsuda | ................ | H04B 1/16 |
| 9,192,961 B2* | 11/2015 | Takahashi | ............ | A61B 8/4494 |
| 9,454,954 B2* | 9/2016 | Hajati | ................... | H01L 41/098 |
| 9,511,393 B2* | 12/2016 | Safai | ..................... | G01N 29/34 |
| 9,757,857 B2* | 9/2017 | Miyazawa | ................. | B25J 9/12 |
| 9,846,145 B2* | 12/2017 | Yoshimura | ........... | A61B 8/4494 |
| 10,211,388 B2* | 2/2019 | Cho | ..................... | H01L 41/047 |
| 10,241,083 B2* | 3/2019 | Schulz | ................ | G01N 29/041 |
| 10,424,719 B2* | 9/2019 | Kiyose | ................. | H01L 41/042 |
| 10,524,764 B2* | 1/2020 | Kiyose | ................. | H01L 41/332 |
| 10,578,614 B2* | 3/2020 | Murdock | ........... | G01N 29/022 |
| 2008/0130921 A1* | 6/2008 | Tokuhisa | ................ | H04R 1/08 381/190 |
| 2009/0322181 A1* | 12/2009 | Machida | .............. | B06B 1/0292 310/300 |
| 2010/0277040 A1 | 11/2010 | Klee et al. | | |
| 2011/0115337 A1* | 5/2011 | Nakamura | ............. | G10K 9/122 310/334 |
| 2014/0104989 A1* | 4/2014 | Matsuda | ........... | G01N 29/0654 367/138 |
| 2015/0273526 A1 | 10/2015 | Tsuruno et al. | | |
| 2020/0029936 A1* | 1/2020 | Sato | ...................... | G10K 11/00 |

FOREIGN PATENT DOCUMENTS

| | | |
|---|---|---|
| JP | 2002-271897 A | 9/2002 |
| JP | 2006-319713 A | 11/2006 |
| JP | 2010-539442 A | 12/2010 |
| JP | 2015-195351 A | 11/2015 |
| JP | 2017-085426 A | 5/2017 |

\* cited by examiner

ULTRASONIC TRANSDUCER HAVING AT LEAST TWO PAIRS OF ELECTRODES SANDWICHING A PIEZOELECTRIC BODY

CROSS-REFERENCE TO RELATED APPLICATIONS

This application is a U.S. National Stage Application of International Application No. PCT/JP2017/013299, filed Mar. 30, 2017, and published in Japanese as WO 2017/175660 A1 on Oct. 12, 2017, which claims priority to Japanese Patent Application No. 2016-076475, filed Apr. 6, 2016. The entire disclosures of the above applications are incorporated herein by reference.

BACKGROUND

Technical Field

The present invention relates to an ultrasonic transducer, an ultrasonic array, an ultrasonic module, an ultrasonic probe, and an ultrasonic apparatus.

Related Art

In the related art, there has been known an ultrasonic transducer that is configured to be capable of transmitting and receiving an ultrasonic wave based on a piezoelectric effect of a piezoelectric layer (for example, JP-A-2002-271897).

The ultrasonic transducer disclosed in JP-A-2002-271897 includes a substrate, a piezoelectric layer provided on the substrate, and a first electrode and a second electrode disposed on the same surface of the piezoelectric layer. In the ultrasonic transducer configured as described above, for example, it is possible to output a potential difference between the first electrode and the second electrode as an electric signal, the potential difference being produced due to a strain of the piezoelectric layer when the ultrasonic transducer receives the ultrasonic wave.

Incidentally, when the ultrasonic transducer receives the ultrasonic wave, a potential difference V between the electrodes is proportional to a distance d between the electrodes, with respect to electric charge Q that is generated on a front surface of the piezoelectric layer due to the strain of the piezoelectric layer (V∝Q×d). In the ultrasonic transducer disclosed in JP-A-2002-271897, it is possible to increase a distance dimension between the electrodes regardless of a thickness of the piezoelectric layer, and thus it is possible to improve receiving sensitivity.

However, the electric charge Q (that is, a strain amount of the piezoelectric layer) that is generated on the front surface of the piezoelectric layer is inversely proportional to the distance d between the electrodes, with respect to the potential difference V between the electrodes (Q∝V/d). Hence, in a case where the ultrasonic wave is transmitted and received by using the ultrasonic transducer in the related art, a problem arises in that it is not possible to compatibly improve a transmission output (transmitting sensitivity) and receiving sensitivity of the ultrasonic wave.

An object of the present invention is to provide, as the following aspect or application example, an ultrasonic transducer having a high transmission output and receiving sensitivity, an ultrasonic array, an ultrasonic module, an ultrasonic probe, and an ultrasonic apparatus.

SUMMARY

An ultrasonic transducer according to an application example includes: a flexible film; and a piezoelectric element that is provided on the flexible film. The piezoelectric element includes a piezoelectric body and a first electrode, a second electrode, a third electrode, and a fourth electrode that are in contact with the piezoelectric body. The first electrode and the second electrode are separated from each other with the piezoelectric body interposed between the first electrode and the second electrode and overlap each other in plan view when viewed in a thickness direction of the piezoelectric body. The third electrode and the fourth electrode are separated from each other with the piezoelectric body interposed between the third electrode and the fourth electrode and overlap each other in the plan view. The first electrode and the third electrode are separated from each other in the plan view. The second electrode and the fourth electrode are separated from each other in the plan view.

In this application example, the piezoelectric element includes the piezoelectric body and the first electrode, the second electrode, the third electrode, and the fourth electrode that are in contact with the piezoelectric body. Of the electrodes, the first electrode and the second electrode are separated from each other with the piezoelectric body interposed therebetween and overlap each other in the plan view when viewed in the thickness direction of the piezoelectric body. In addition, the third electrode and the fourth electrode are separated from each other with the piezoelectric body interposed therebetween and overlap each other in the plan view. In addition, in the plan view, the first electrode and the third electrode are separated from each other, and the second electrode and the fourth electrode are separated from each other.

In the ultrasonic transducer configured as described above, while it is possible to decrease a distance between the first electrode and the second electrode and a distance between the third electrode and the fourth electrode, it is possible to increase a distance between the first electrode and the third electrode and a distance between the second electrode and the fourth electrode. In this manner, it is possible to improve a transmission output and receiving sensitivity of the ultrasonic transducer at the same time.

In other words, when an ultrasonic wave is transmitted by using the ultrasonic transducer, a voltage is applied between the first electrode and the second electrode, a voltage is applied between the third electrode and the fourth electrode, and the distances between the electrodes are decreased as described above. In this manner, it is possible to improve the transmission output of the ultrasonic transducer.

On the other hand, a potential difference produced between the first electrode and the third electrode (a potential difference produced between the second electrode and the fourth electrode) due to a strain of the piezoelectric body is detected, and thus it is possible to receive the ultrasonic wave. In this case, the distance between the first electrode and the third electrode (the second electrode and the fourth electrode) is increased, and thereby it is possible to improve the receiving sensitivity as described above.

As described above, according to this application example, it is possible to provide the ultrasonic transducer having a high transmission output and receiving sensitivity.

In addition, according to this application example, when the ultrasonic wave is received, the first electrode and the second electrode are short-circuited, and the third electrode and the fourth electrode are short-circuited. In this manner, it is possible to easily perform impedance matching between the ultrasonic transducer and an external circuit that is connected to the ultrasonic transducer. In other words, the electrodes are short-circuited as described above, and thereby a capacitor formed by the first electrode and the third electrode and a capacitor formed by the second electrode and the fourth electrode are configured to be connected in parallel. Hence, it is possible to more increase capacitance of the ultrasonic transducer of this application example, compared to an ultrasonic transducer in the related art, which includes two electrodes that are disposed to be separated from each other on one surface of the piezoelectric body described above. In this manner, it is possible to suppress an influence of stray capacitance of the external circuit, and thus it is possible to easily perform the impedance matching with the external circuit.

In the ultrasonic transducer according to this application example, it is preferable that the piezoelectric element further includes a fifth electrode and a sixth electrode that are in contact with the piezoelectric body, the fifth electrode and the sixth electrode are separated from each other with the piezoelectric body interposed between the fifth electrode and the sixth electrode and overlap each other in the plan view, the fifth electrode is positioned between the first electrode and the third electrode, and the sixth electrode is positioned between the second electrode and the fourth electrode.

In this application example, the piezoelectric element includes the fifth electrode and the sixth electrode which overlap each other in the plan view, the fifth electrode is positioned between the first electrode and the third electrode, and the sixth electrode is positioned between the second electrode and the fourth electrode.

In this configuration, when the ultrasonic wave is received, the first electrode, the second electrode, the third electrode, and the fourth electrode are short-circuited, and the fifth electrode and the sixth electrode are short-circuited. In this manner, a capacitor formed by the first electrode and the fifth electrode, a capacitor formed by the third electrode and the fifth electrode, a capacitor formed by the second electrode and the sixth electrode, and a capacitor formed by the fourth electrode and the sixth electrode can be configured to be connected in parallel. In this manner, it is possible to more increase the stray capacitance of the ultrasonic transducer, and it is possible to more easily perform the impedance matching with the external circuit.

In the ultrasonic transducer according to this application example, it is preferable that a distance between the first electrode and the fourth electrode is longer than a distance between the first electrode and the third electrode.

In this application example, since the distance between the first electrode and the fourth electrode is longer than the distance between the first electrode and the third electrode, it is possible to suppress short-circuit of the first electrode and the fourth electrode. For example, when the ultrasonic wave is received, it is possible to suppress the short circuit of the first electrode and the fourth electrode even in a case where the potential difference is produced between the first electrode and the third electrode and between the second electrode and the fourth electrode, and thus it is possible to receive the ultrasonic wave.

In the ultrasonic transducer according to this application example, it is preferable that an end surface of the first electrode, which is opposite to the third electrode, overlaps an end surface of the second electrode, which is opposite to the fourth electrode, in the plan view.

In this application example, the end surface of the first electrode, which is opposite to the third electrode, overlaps the end surface of the second electrode, which is opposite to the fourth electrode, in the plan view. In this configuration, for example, when a voltage is applied between the first electrode and the second electrode, it is possible to more effectively apply the voltage, compared to a case where the end surfaces of the first electrode and the second electrode do not overlap each other in the plan view.

An ultrasonic array according to another application example includes: a plurality of ultrasonic transducers, each of which includes a flexible film and a piezoelectric element that is provided on the flexible film. The piezoelectric element includes a piezoelectric body and a first electrode, a second electrode, a third electrode, and a fourth electrode that are in contact with the piezoelectric body. The first electrode and the second electrode are separated from each other with the piezoelectric body interposed between the first electrode and the second electrode and overlap each other in plan view when viewed in a thickness direction of the piezoelectric body. The third electrode and the fourth electrode are separated from each other with the piezoelectric body interposed between the third electrode and the fourth electrode and overlap each other in the plan view. The first electrode and the third electrode are separated from each other in the plan view. The second electrode and the fourth electrode are separated from each other in the plan view.

In this application example, the piezoelectric element includes the piezoelectric body and the first electrode, the second electrode, the third electrode, and the fourth electrode that are in contact with the piezoelectric body. Of the electrodes, the first electrode and the second electrode are separated from each other with the piezoelectric body interposed therebetween and overlap each other in the plan view when viewed in the thickness direction of the piezoelectric body. In addition, the third electrode and the fourth electrode are separated from each other with the piezoelectric body interposed therebetween and overlap each other in the plan view. In addition, the first electrode and the third electrode are separated from each other in the plan view, and the second electrode and the fourth electrode are separated from each other in the plan view.

In the ultrasonic array configured as described above, similar to the ultrasonic transducer of the application example described above, while it is possible to decrease a distance between the first electrode and the second electrode and a distance between the third electrode and the fourth electrode, it is possible to increase a distance between the first electrode and the third electrode and a distance between the second electrode and the fourth electrode. In this manner, it is possible to improve a transmission output and receiving sensitivity of the ultrasonic transducer.

In addition, it is possible to transmit and receive the ultrasonic wave by using the ultrasonic transducers. Therefore, it is possible to more increase the number of both of transmitting and receiving ultrasonic transducers per unit area, and thus it is possible to improve the transmission output and the receiving sensitivity of the ultrasonic wave, compared to an ultrasonic array including a transmitting-dedicated ultrasonic transducer and a receiving-dedicated ultrasonic transducer.

An ultrasonic module according to still another application example includes: an ultrasonic transducer that includes a flexible film and a piezoelectric element which is provided on the flexible film; and a circuit substrate that is connected to the piezoelectric element. The piezoelectric element includes a piezoelectric body and a first electrode, a second electrode, a third electrode, and a fourth electrode that are in contact with the piezoelectric body. The first electrode and the second electrode are separated from each other with the piezoelectric body interposed between the first electrode and the second electrode and overlap each other in plan view when viewed in a thickness direction of the piezoelectric body. The third electrode and the fourth electrode are separated from each other with the piezoelectric body interposed between the third electrode and the fourth electrode and overlap each other in the plan view. The first electrode and the third electrode are separated from each other in the plan view. The second electrode and the fourth electrode are separated from each other in the plan view.

The ultrasonic module of this application example includes the ultrasonic transducer, which includes the piezoelectric element, and the circuit substrate connected to the piezoelectric element. Of the components, the piezoelectric element includes the piezoelectric body and the first electrode, the second electrode, the third electrode, and the fourth electrode that are in contact with the piezoelectric body. Of the electrodes, the first electrode and the second electrode are separated from each other with the piezoelectric body interposed therebetween and overlap each other in the plan view when viewed in the thickness direction of the piezoelectric body. In addition, the third electrode and the fourth electrode are separated from each other with the piezoelectric body interposed therebetween and overlap each other in the plan view. In addition, the first electrode and the third electrode are separated from each other in the plan view, and the second electrode and the fourth electrode are separated from each other in the plan view.

In the ultrasonic module configured as described above, similar to the ultrasonic transducer of the application example described above, while it is possible to decrease a distance between the first electrode and the second electrode and a distance between the third electrode and the fourth electrode, it is possible to increase a distance between the first electrode and the third electrode and a distance between the second electrode and the fourth electrode. In this manner, it is possible to improve the transmission output and the receiving sensitivity of the ultrasonic transducer.

In the ultrasonic module of this application example, it is preferable that the circuit substrate includes a switching unit that switches a connection state between a first connection state in which the first electrode and the third electrode are connected to each other and the second electrode and the fourth electrode are connected to each other and a second connection state in which the first electrode and the second electrode are connected to each other and the third electrode and the fourth electrode are connected to each other.

In this application example, the switching unit switches the connection state between the first connection state in which the first electrode and the third electrode are connected to each other and the second electrode and the fourth electrode are connected to each other and the second connection state in which the first electrode and the second electrode are connected to each other and the third electrode and the fourth electrode are connected to each other.

In the first connection state, the first electrode and the third electrode are connected to each other, that is, are short-circuited, and the second electrode and the fourth electrode are short-circuited. For example, when the ultrasonic wave is received, in the first connection state, a voltage is applied to the short-circuited first and third electrodes. In this manner, it is possible to produce potential differences between the first electrode and the second electrode and between the third electrode and the fourth electrode, and it is possible to improve the transmission output as described above.

In addition, in the second connection state, the first electrode and the second electrode are short-circuited, and the third electrode and the fourth electrode are short-circuited. In the second connection state, when the ultrasonic wave is received, a potential difference produced between the first electrode and the third electrode (a potential difference produced between the second electrode and the fourth electrode) due to a strain of the piezoelectric body is output as an electric signal. Therefore, detection of the electric signal enables the receiving sensitivity of the ultrasonic wave to be improved as described above.

As described above, according to this application example, it is possible to provide the ultrasonic module having the high transmission output and receiving sensitivity.

An ultrasonic probe according to still another application example includes: an ultrasonic transducer that includes a flexible film and a piezoelectric element that is provided on the flexible film; and a housing that accommodates the ultrasonic transducer. The piezoelectric element includes a piezoelectric body and a first electrode, a second electrode, a third electrode, and a fourth electrode that are in contact with the piezoelectric body. The first electrode and the second electrode are separated from each other with the piezoelectric body interposed between the first electrode and the second electrode and overlap each other in plan view when viewed in a thickness direction of the piezoelectric body. The third electrode and the fourth electrode are separated from each other with the piezoelectric body interposed between the third electrode and the fourth electrode and overlap each other in the plan view. The first electrode and the third electrode are separated from each other in the plan view. The second electrode and the fourth electrode are separated from each other in the plan view.

The ultrasonic probe of this application example includes the ultrasonic transducer and the housing that accommodates the ultrasonic transducer. Of the components, the ultrasonic transducer includes the piezoelectric element, and the piezoelectric element includes the piezoelectric body and the first electrode, the second electrode, the third electrode, and the fourth electrode that are in contact with the piezoelectric body. Of the electrodes, the first electrode and the second electrode are separated from each other with the piezoelectric body interposed therebetween and overlap each other in the plan view when viewed in the thickness direction of the piezoelectric body. In addition, the third electrode and the fourth electrode are separated from each other with the piezoelectric body interposed therebetween and overlap each other in the plan view. In addition, the first electrode and the third electrode are separated from each other in the plan view, and the second electrode and the fourth electrode are separated from each other in the plan view.

In the ultrasonic probe configured as described above, similar to the ultrasonic transducer of the application example described above, while it is possible to decrease a distance between the first electrode and the second electrode and a distance between the third electrode and the fourth electrode, it is possible to increase a distance between the first electrode and the third electrode and a distance between the second electrode and the fourth electrode. In this manner, it is possible to improve the transmission output and the receiving sensitivity of the ultrasonic transducer.

An ultrasonic apparatus according to still another application example includes: an ultrasonic transducer that includes a flexible film and a piezoelectric element which is provided on the flexible film; and a controller that controls the ultrasonic transducer. The piezoelectric element includes a piezoelectric body and a first electrode, a second electrode, a third electrode, and a fourth electrode that are in contact with the piezoelectric body. The first electrode and the second electrode are separated from each other with the piezoelectric body interposed between the first electrode and the second electrode and overlap each other in plan view when viewed in a thickness direction of the piezoelectric body. The third electrode and the fourth electrode are separated from each other with the piezoelectric body interposed between the third electrode and the fourth electrode and overlap each other in the plan view. The first electrode and the third electrode are separated from each other in the plan view. The second electrode and the fourth electrode are separated from each other in the plan view.

The ultrasonic apparatus of this application example includes the ultrasonic transducer and the controller that controls the ultrasonic transducer. Of the components, the ultrasonic transducer includes the piezoelectric element, and the piezoelectric element includes the piezoelectric body and the first electrode, the second electrode, the third electrode, and the fourth electrode that are in contact with the piezoelectric body. Of the electrodes, the first electrode and the second electrode are separated from each other with the piezoelectric body interposed therebetween and overlap each other in the plan view when viewed in the thickness direction of the piezoelectric body. In addition, the third electrode and the fourth electrode are separated from each other with the piezoelectric body interposed therebetween and overlap each other in the plan view. In addition, the first electrode and the third electrode are separated from each other in the plan view, and the second electrode and the fourth electrode are separated from each other in the plan view.

In the ultrasonic apparatus configured as described above, similar to the ultrasonic transducer of the application example described above, while it is possible to decrease a distance between the first electrode and the second electrode and a distance between the third electrode and the fourth electrode, it is possible to increase a distance between the first electrode and the third electrode and a distance between the second electrode and the fourth electrode. In this manner, it is possible to improve the transmission output and the receiving sensitivity of the ultrasonic transducer.

It is preferable that the ultrasonic apparatus of this application example further includes a switching unit that switches a connection state between a first connection state in which the first electrode and the third electrode are connected to each other and the second electrode and the fourth electrode are connected to each other and a second connection state in which the first electrode and the second electrode are connected to each other and the third electrode and the fourth electrode are connected to each other.

In this application example, the switching unit switches the connection state between the first connection state in which the first electrode and the third electrode are connected to each other and the second electrode and the fourth electrode are connected to each other and the second connection state in which the first electrode and the second electrode are connected to each other and the third electrode and the fourth electrode are connected to each other.

In addition, in the first connection state, the first electrode and the third electrode are short-circuited, and the second electrode and the fourth electrode are short-circuited. For example, when the ultrasonic wave is received, in the first connection state, a voltage is applied to the short-circuited first and third electrodes. In this manner, it is possible to produce potential differences between the first electrode and the second electrode and between the third electrode and the fourth electrode, and it is possible to improve the transmission output as described above.

In addition, in the second connection state, the first electrode and the second electrode are short-circuited, and the third electrode and the fourth electrode are short-circuited. In the second connection state, when the ultrasonic wave is received, a potential difference produced between the first electrode and the third electrode (a potential difference produced between the second electrode and the fourth electrode) due to a strain of the piezoelectric body is output as an electric signal. Therefore, detection of the electric signal enables the receiving sensitivity of the ultrasonic wave to be improved as described above.

As described above, according to this application example, it is possible to provide the ultrasonic apparatus having the high transmission output and receiving sensitivity.

In the ultrasonic apparatus of this application example, it is preferable that the controller includes a switching control unit that controls the switching unit, switches the connection state to the first connection state when the ultrasonic wave is transmitted, and switches the connection state to the second connection state when the ultrasonic wave is received.

In this application example, the controller includes the switching control unit causes the switching unit to switch the connection state to the first connection state when the ultrasonic wave is transmitted and causes the switching unit to switch the connection state to the second connection state when the ultrasonic wave is received. In this configuration, it is possible to appropriately set the connection state of the electrodes by the switching unit when the ultrasonic wave is transmitted and received.

In the ultrasonic apparatus of this application example, it is preferable that the controller includes a polarization control unit that executes a first polarization process in which a first polarization voltage is applied between the first electrode and the second electrode and between the third electrode and the fourth electrode.

In this application example, the polarization control unit executes the first polarization process in which the respective first polarization voltages are applied between the first electrode and the second electrode and between the third electrode and the fourth electrode.

As described above, when the ultrasonic wave is transmitted, the respective voltages are applied between the first electrode and the second electrode and between the third electrode and the fourth electrode, and thereby it is possible to improve the transmission output of the ultrasonic transducer. In this application example, the first polarization process is executed such that an electric field in the thickness direction is applied to the piezoelectric body, and thereby it is possible to change a polarization state of the piezoelectric body into a state that is suitable for transmitting the ultrasonic wave. Hence, the execution of the first polarization process enables the transmission output of the ultrasonic transducer to be more improved, and thus enables accuracy of ultrasonic measurement in the ultrasonic apparatus to be more improved.

In the ultrasonic apparatus of this application example, it is preferable that the controller includes a polarization control unit that executes a second polarization process in which a second polarization voltage is applied between the first electrode and the third electrode and between the second electrode and the fourth electrode.

In this application example, the polarization control unit executes the second polarization process in which the respective second polarization voltages are applied between the first electrode and the second electrode and between the third electrode and the fourth electrode.

As described above, when the ultrasonic wave is transmitted, the respective voltages are applied between the first electrode and the third electrode and between the second electrode and the fourth electrode, and thereby it is possible to improve the receiving sensitivity of the ultrasonic transducer. In this application example, the second polarization process is executed such that an electric field in a direction intersecting with the thickness direction is applied to the piezoelectric body, and thereby it is possible to change a polarization state of the piezoelectric body into a state that is suitable for receiving the ultrasonic wave. Hence, the execution of the second polarization process enables the receiving sensitivity of the ultrasonic transducer to be more improved, and thus enables accuracy of ultrasonic measurement in the ultrasonic apparatus to be more improved.

In the ultrasonic apparatus of this application example, it is preferable that the controller includes a transmitting/receiving control unit that controls the ultrasonic transducer such that the ultrasonic wave is transmitted and received, the switching control unit that controls the switching unit, switches the connection state to the first connection state when the ultrasonic wave is transmitted, and switches the connection state to the second connection state when the ultrasonic wave is received, and the polarization control unit that executes the first polarization process in which the respective first polarization voltages are applied between the first electrode and the second electrode and between the third electrode and the fourth electrode, and the second polarization process in which the respective second polarization voltages are applied between the first electrode and the third electrode and between the second electrode and the fourth electrode. It is preferable that the switching control unit switches the connection state to the first connection state, and the polarization control unit executes the first polarization process. It is preferable that the transmitting/receiving control unit transmits the ultrasonic wave from the ultrasonic transducer and the switching control unit switches the connection state to the second connection state. It is preferable that the polarization control unit executes the second polarization process, and the transmitting/receiving control unit receives the ultrasonic wave by using the ultrasonic transducer.

In this application example, since it is possible to transmit the ultrasonic wave after the ultrasonic apparatus switches the connection state to the first connection state and executes the first polarization process, it is possible to improve the transmission output of the ultrasonic wave. In addition, since it is possible to transmit the ultrasonic wave after the ultrasonic apparatus switches the connection state to the second connection state and executes the second polarization process, it is possible to improve the receiving sensitivity of the ultrasonic wave. Hence, the ultrasonic apparatus of this application example can execute the ultrasonic measurement with high accuracy.

DETAILED DESCRIPTION

First Embodiment

Figure 1:
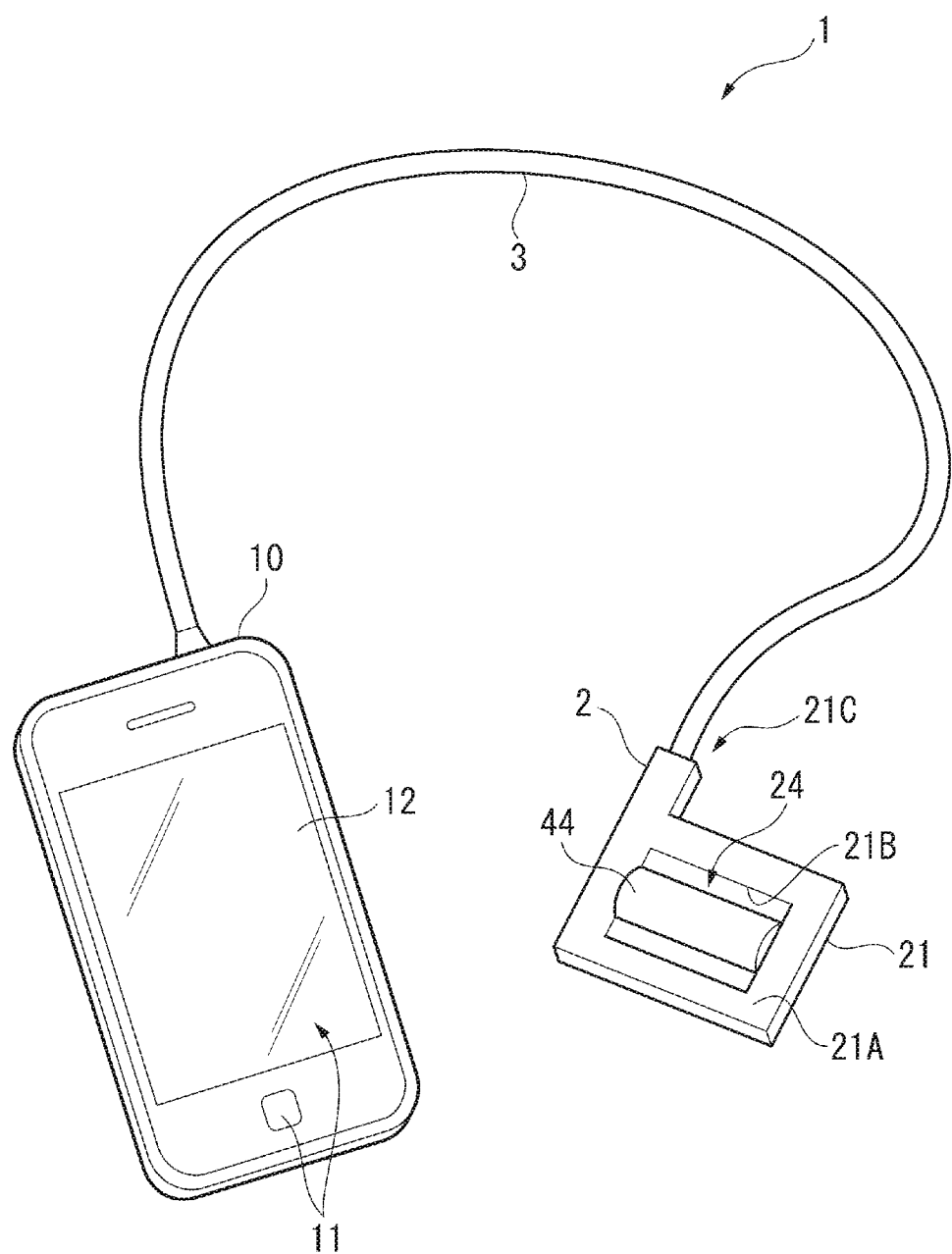
FIG. 1 is a perspective view showing a schematic configuration of an ultrasonic apparatus of a first embodiment.
Figure 2:
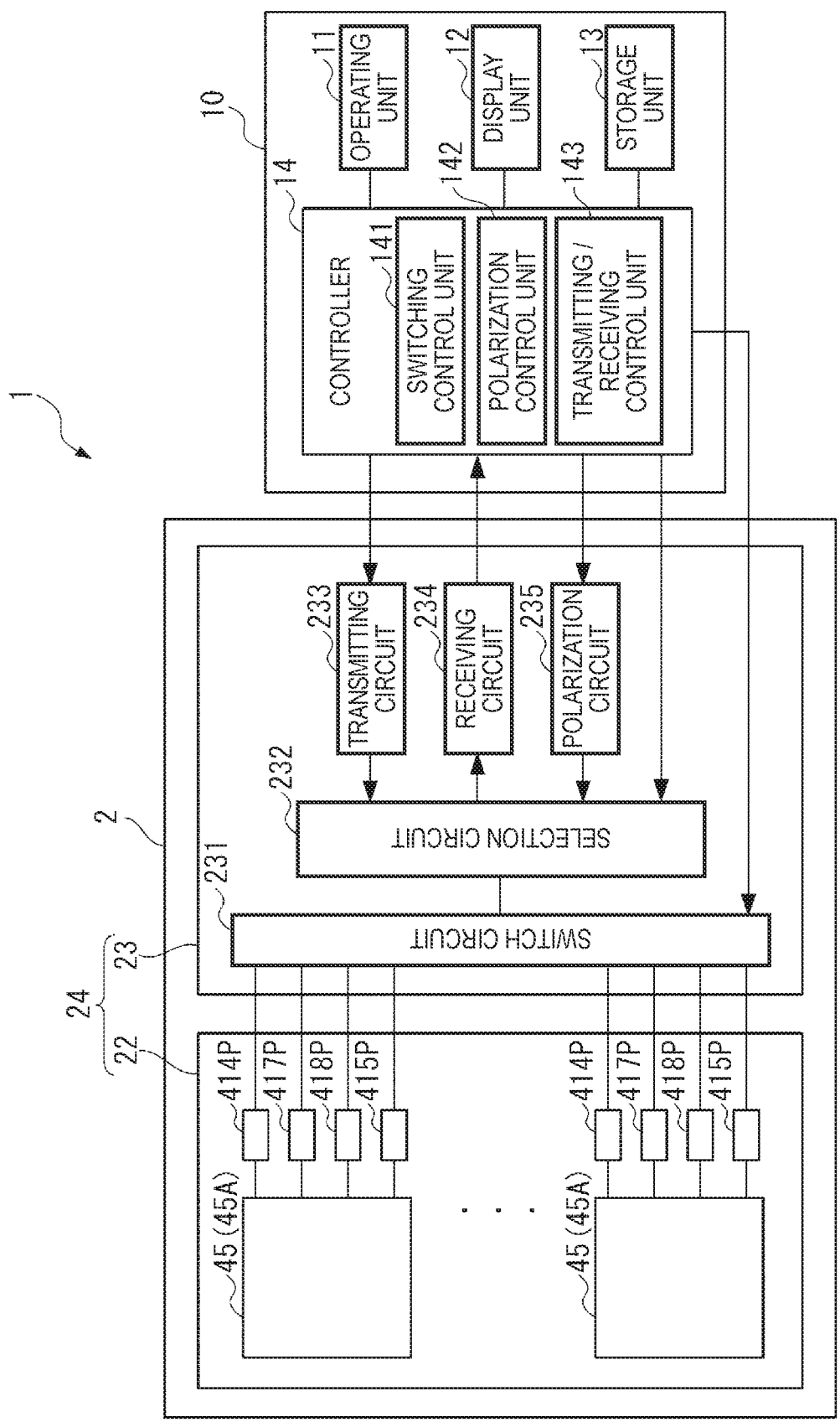
FIG. 2 is a block diagram illustrating a schematic configuration of the ultrasonic apparatus of the first embodiment.

Hereinafter, an ultrasonic apparatus according to a first embodiment will be described with reference to figures.
Configuration of Ultrasonic Apparatus FIG. 1 is a perspective view illustrating a schematic configuration of an ultrasonic apparatus 1 according to the embodiment. FIG. 2 is a block diagram illustrating a schematic configuration of the ultrasonic apparatus 1.

As shown in FIG. 1, the ultrasonic apparatus 1 of the embodiment includes an ultrasonic probe 2 and a control device 10 that is electrically connected to the ultrasonic probe 2 via a cable 3.

In the ultrasonic apparatus 1, the ultrasonic probe 2 comes into contact with a surface of a living body (for example, a human body) and an ultrasonic wave is transmitted into the living body from the ultrasonic probe 2. In addition, an ultrasonic wave reflected from an organ in the living body is received by the ultrasonic probe 2 and, for example, an internal tomographic image of the inside of the living body is acquired, based on a received signal thereof, or a state (for example, bloodstream or the like) of the organ in the living body is measured.
Configuration of Ultrasonic Probe The ultrasonic probe 2 includes a housing 21 (refer to FIG. 1), an ultrasonic device 22 (refer to FIG. 2), a circuit substrate 23 (refer to FIG. 2) in which a driver circuit or the like for controlling the ultrasonic device 22 is provided. The ultrasonic device 22 is configured of an ultrasonic sensor 24 corresponding to an ultrasonic module by the circuit substrate 23 and is accommodated in the housing 21.
Configuration of Housing As shown in FIG. 1, the housing 21 is formed to have a rectangular box-shape in plan view and has a sensor window 21B, through which a part of the ultrasonic device 22 is exposed, on one surface (sensor surface 21A) orthogonal to a thickness direction of the housing. In addition, a part (side surface in an example shown in FIG. 1) of the housing 21 is provided with a passing hole 21C of the cable 3, and the cable 3 is connected to the circuit substrate 23 inside the housing 21 from the passing hole 21C. In addition, a gap between the cable 3 and the passing hole 21C is filled with a resin material or the like and, thus, secures a waterproof property.

In the embodiment, a configurational example in which the ultrasonic probe 2 and the control device 10 are connected to each other by using the cable 3 is employed; however, the configuration is not limited thereto and, for example, the ultrasonic probe 2 and the control device 10 may be connected to each other through wireless communication, or various types of configurations of the control device 10 may be provided in the ultrasonic probe 2.

Configuration of Ultrasonic Device

Figure 3:
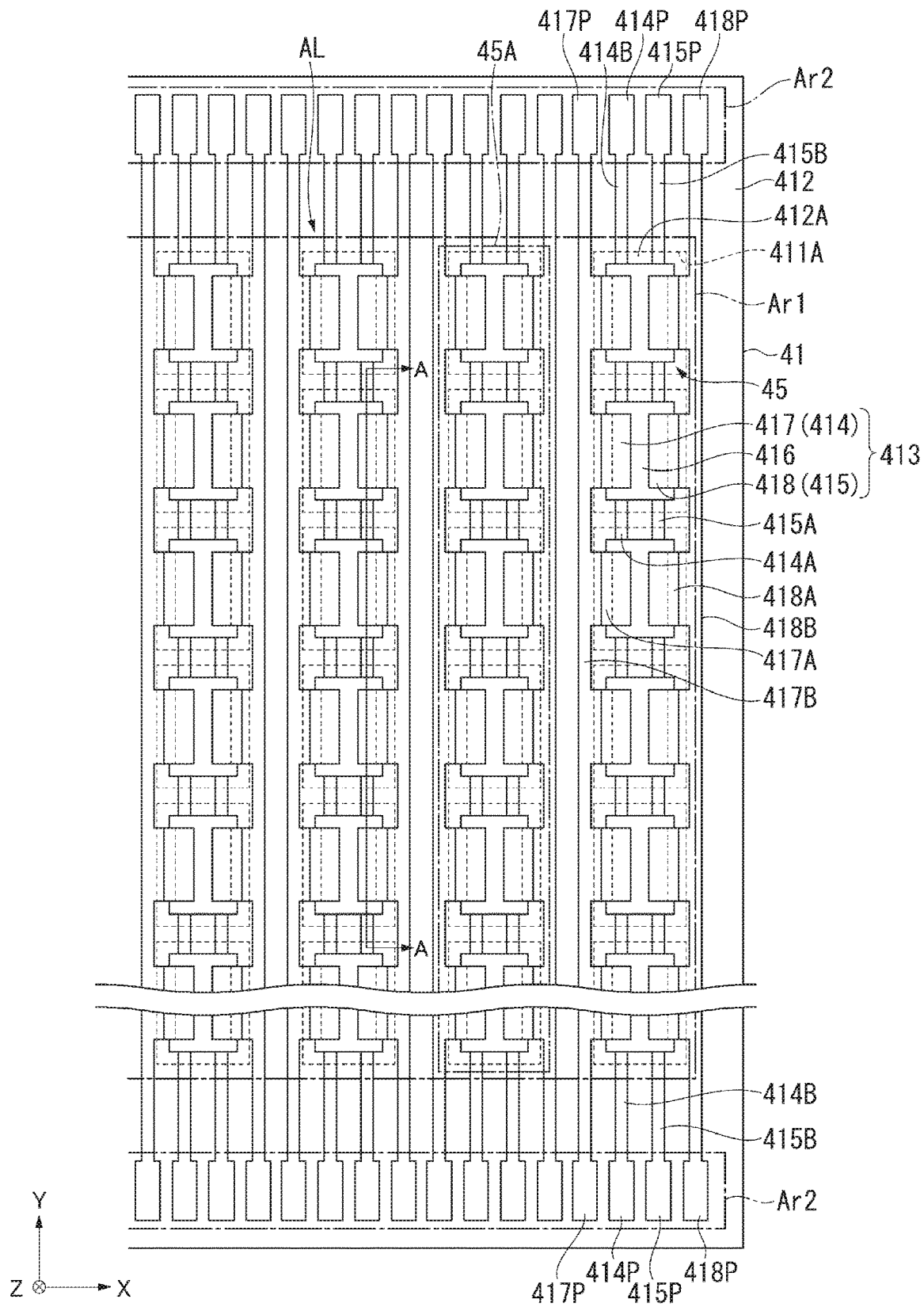
FIG. 3 is a plan view showing a schematic configuration of an element substrate in an ultrasonic device of the first embodiment.
Figure 4:
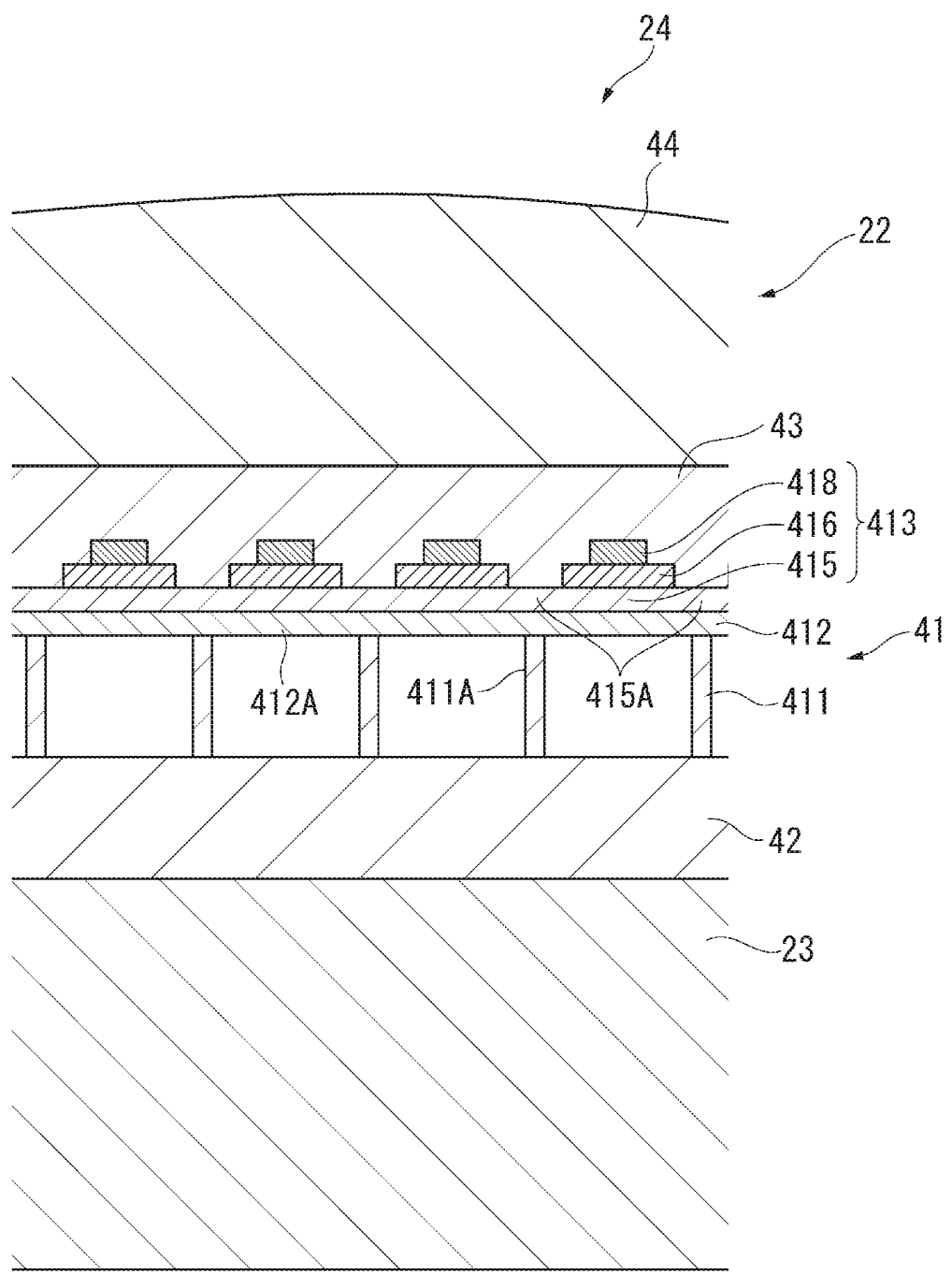
FIG. 4 is a sectional view of an ultrasonic sensor cut along line A-A in FIG. 3.
Figure 5:
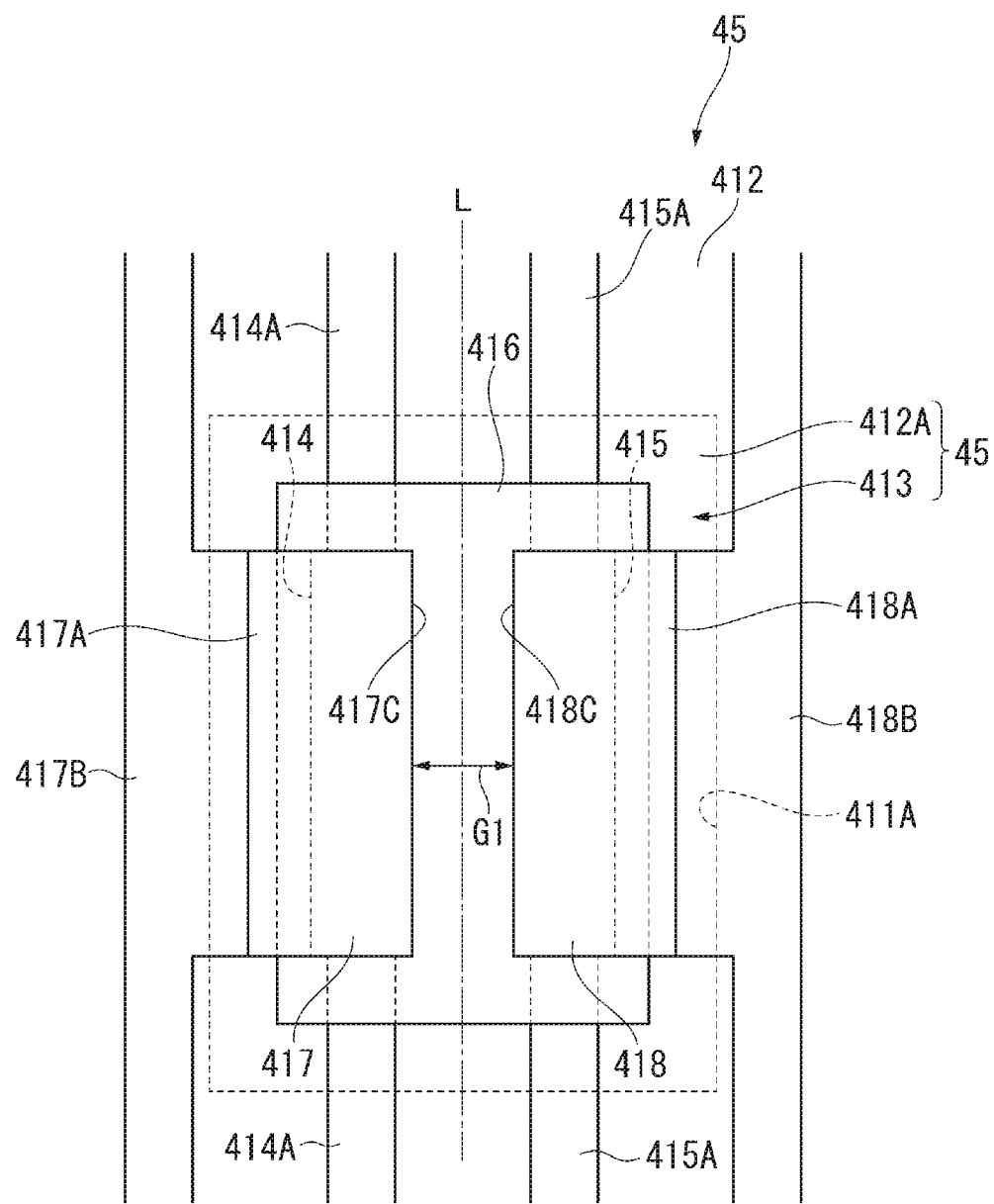
FIG. 5 is a plan view showing a schematic configuration of an ultrasonic transducer of the first embodiment.

FIG. 3 is a plan view showing an element substrate 41 in an ultrasonic device 22 when viewed from a side of an acoustic lens 44. FIG. 4 is a sectional view of the ultrasonic sensor 24 cut along line A-A in FIG. 3. FIG. 5 is a plan view schematically showing an ultrasonic transducer 45 when viewed from the side of the acoustic lens 44.

As shown in FIG. 4, the ultrasonic device 22 constituting the ultrasonic sensor 24 is configured to have the element substrate 41, a sealing plate 42, an acoustic matching layer 43, and the acoustic lens 44. As shown in FIG. 3, a plurality of ultrasonic transducers 45 that transmit and receive the ultrasonic wave are disposed in a matrix shape on the element substrate 41. An ultrasonic array AL is configured of the plurality of ultrasonic transducers 45.

Configuration of Element Substrate

The element substrate 41 includes a substrate main body 411 and a vibration film 412 stacked on the substrate main body 411. The central region of the element substrate 41 is an array region Ar1 in which the ultrasonic array AL is formed.

For example, the substrate main body 411 is a semiconductor substrate made of Si or the like. The substrate main body 411 is provided with openings 411A corresponding to the respective ultrasonic transducers 45, in the array region Ar1. In addition, the opening 411A is covered and opened with the vibration film 412 provided on the side of the acoustic lens 44 (+Z side) of the substrate main body 411.

For example, the vibration film 412 is made of $SiO_2$ or a laminated body of $SiO_2$ and $ZrO_2$ and is provided to cover the entirety of the substrate main body 411 on a +Z side. The vibration film 412 has a sufficiently smaller dimension than a thickness dimension of the substrate main body 411. In a case where the substrate main body 411 is made of Si, and the vibration film 412 is made of $SiO_2$, the substrate main body 411 is subjected to an oxidation treatment, and thereby it is possible to easily form the vibration film 412 having a predetermined dimension. In this case, the substrate main body 411 is subjected to an etching process with the vibration film 412 made of $SiO_2$ as an etching stopper, and thereby it is possible to easily form the opening 411A.

In addition, on the vibration film 412 that blocks the opening 411A, a piezoelectric element 413 that is configured to have a first lower electrode 414, a second lower electrode 415, a piezoelectric film 416, a first upper electrode 417, and a second upper electrode 418 (refer to FIGS. 4 and 5). Here, a part that blocks the opening 411A of the vibration film 412 is a flexible film 412A that is deformed when an ultrasonic wave is transmitted and received. One ultrasonic transducer 45 is configured to have the flexible film 412A and the piezoelectric element 413. The ultrasonic transducer 45 will be described below.

In addition, In the embodiment, as shown in FIG. 3, a plurality of ultrasonic transducers 45 are arranged in a predetermined array region Ar1 of the element substrate 41 in a Y direction (slice direction) and an X direction (scan direction), which intersects with (in the embodiment, orthogonal to) the Y direction, and constitute the ultrasonic array AL.

In addition, an ultrasonic transducer group 45A constituting one transmitting/receiving channel is configured to have the ultrasonic transducers 45 aligned in the Y direction, and a plurality of ultrasonic transducer groups 45A aligned in the X direction constitute a one-dimensional array structure. In other words, the ultrasonic array AL is a one-dimensional array that is configured to have a plurality of transmitting/receiving channels that are disposed in the X direction.

Here, as shown in FIG. 3, the first lower electrodes 414 of the plurality of ultrasonic transducers 45 which constitute the ultrasonic transducer group 45A are connected to one another. In other words, the first lower electrodes 414 of the ultrasonic transducers 45 adjacent in the Y direction are connected to each other with a first lower electrode line 414A. In addition, the first lower electrodes 414 of the ultrasonic transducers 45 disposed at both ends in the Y direction are connected to first lower electrode pads 414P formed in a terminal region Ar2 outside the array region Ar1, with first lower leading lines 414B. The first lower electrode pad 414P is connected to a switch circuit 231 (to be described below) of the circuit substrate 23.

Similarly, among the plurality of ultrasonic transducers 45 constituting the ultrasonic transducer group 45A, the second lower electrodes 415 of the adjacent ultrasonic transducers 45 are connected to one another with a second lower electrode line 415A. In addition, the second lower electrodes 415 of the ultrasonic transducers 45 disposed at both ends in the Y direction are connected to second lower electrode pads 415P formed in the terminal region Ar2, with second lower leading lines 415B. The second lower electrode pad 415P is connected to the circuit substrate 23.

On the other hand, the first upper electrodes 417 of the plurality of ultrasonic transducers 45 constituting the ultrasonic transducer group 45A are connected to first upper electrode pads 417P formed in the terminal region Ar2, with first upper connection electrodes 417A and a first upper leading line 417B. In other words, the first upper connection electrode 417A is led from the first upper electrode 417 in a −X direction and is connected to the first upper leading line 417B. The first upper leading line 417B is led to the terminal region Ar2 and is connected to the first upper electrode pad 417P in the Y direction.

Similarly, the second upper electrodes 418 of the plurality of ultrasonic transducers 45 constituting the ultrasonic transducer group 45A are connected to second upper electrode pads 418P formed in the terminal region Ar2, with second upper connection electrodes 418A and a second upper leading line 418B. In other words, the second upper connection electrode 418A is led from the second upper electrode 418 in a +X direction and is connected to the second upper leading line 418B. The second upper leading line 418B is led to the terminal region Ar2 and is connected to the second upper electrode pad 418P in the Y direction.

Configuration of Sealing Plate, Acoustic Matching Layer, and Acoustic Lens

The sealing plate 42 is provided for reinforcing the strength of the element substrate 41, for example, is configured of a metal plate such as alloy 42, a semiconductor substrate, or the like, and is bonded to the element substrate 41. A material or a thickness of the sealing plate 42 influences frequency characteristics of the ultrasonic transducer 45, and thus it is preferable to set the material or the thickness based on the center frequency of the ultrasonic wave that is transmitted and received.

As shown in FIG. 4, the acoustic matching layer 43 is provided on a surface of the element substrate 41 on an opposite side to the sealing plate 42. Specifically, a gap between the element substrate 41 and the acoustic lens 44 is filled with the acoustic matching layer 43, and the acoustic matching layer is formed to have a predetermined thickness dimension from a front surface of the substrate main body 411.

As shown in FIG. 1, the acoustic lens 44 is provided on the acoustic matching layer 43 and is exposed from the sensor window 21B of the housing 21 to the outside. The acoustic lens 44 has a cylindrical shape with a surface thereof on a +Z side is curved in the Y direction (slice direction).

The acoustic matching layer 43 and the acoustic lens 44 efficiently propagates, to the living body which is the measurement target, the ultrasonic waves transmitted from the ultrasonic transducer 45, and efficiently propagates, to the ultrasonic transducer 45, the ultrasonic waves reflected from the living body. Therefore, the acoustic matching layer 43 and the acoustic lens 44 is set to have intermediate acoustic impedance between the acoustic impedance of the ultrasonic transducer 45 of the element substrate 41 and the acoustic impedance of the living body. For example, a material for such acoustic impedance can include silicone or the like.

Configuration of Ultrasonic Transducer

Figure 6:
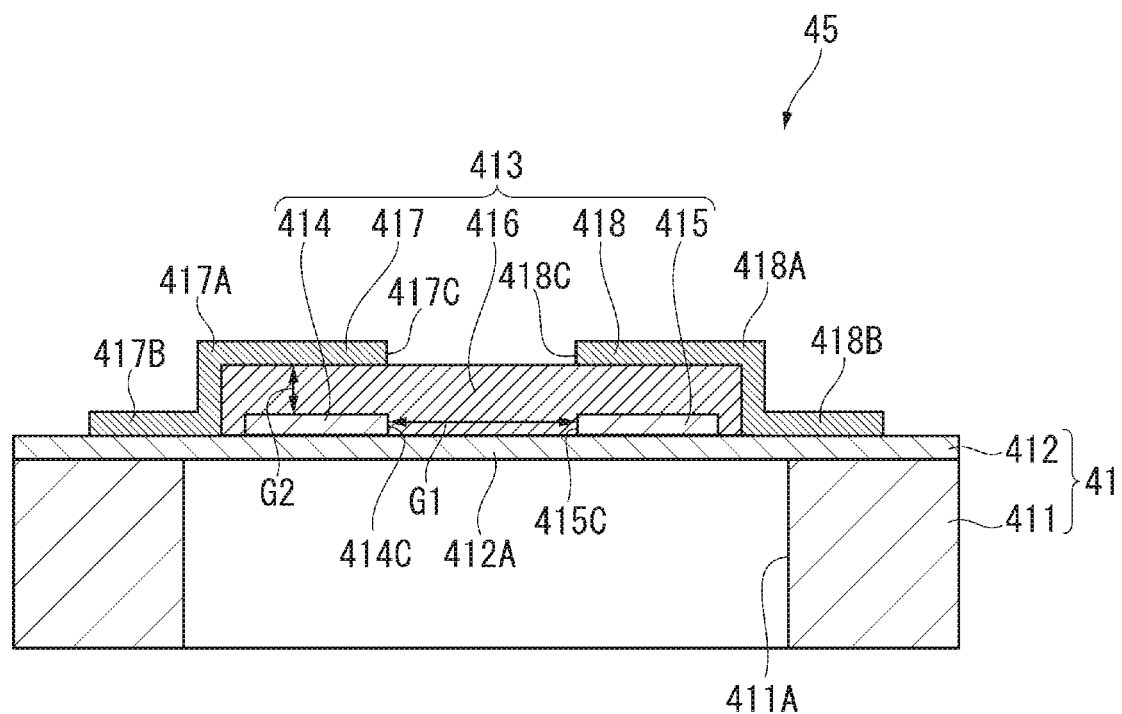
FIG. 6 is a sectional view showing a schematic configuration of the ultrasonic transducer of the first embodiment.
Figure 6:
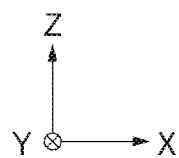

FIG. 6 is a sectional view schematically showing a cross section of the ultrasonic transducer.

The ultrasonic transducer 45 is configured to include the flexible film 412A and the piezoelectric element 413 which is provided on the flexible film 412A.

The flexible film 412A is a part that blocks the opening 411A of the substrate main body 411 in the vibration film 412. The flexible film 412A has a planar shape according to an opening shape of the opening 411A in plan view when viewed from the Z direction. In other words, a natural frequency of the flexible film 412A is a value obtained depending on the opening shape. In other words, it is possible to adjust a frequency of the ultrasonic wave that is transmitted and received by the ultrasonic transducer 45 depending on the shape of the opening 411A.

The piezoelectric element 413 is configured to include the first lower electrode 414, the second lower electrode 415, the piezoelectric film 416, the first upper electrode 417, and the second upper electrode 418. The electrodes 414, 415, 417, and 418 are in contact with the piezoelectric film 416 and are separated from each other.

The first lower electrode 414 corresponds to a first electrode and is provided at a position at which the first lower electrode overlaps the piezoelectric film 416 on a surface of the flexible film 412A on the +Z side in the plan view when viewed in the Z direction (a thickness direction of the piezoelectric film 416) (hereinafter, simply referred to as plan view) (refer to FIG. 5). In the embodiment, the first lower electrode 414 has a substantially rectangular planar shape as shown in FIG. 5, and an end surface 414C on a +X side is separated from the second lower electrode 415 by a gap G1 having a predetermined dimension in the X direction. In other words, the first lower electrode 414 is connected to a first lower electrode 414 of an adjacent ultrasonic transducer 45 in the Y direction, with the first lower electrode line 414A.

For example, the first lower electrode 414 is formed by an electrode material having conductivity such as Ir, Pt, IrOx, Ti, or TiOx. At this time, a front surface of the vibration film 412 on the +Z side is configured to contain $ZrO_2$, which is a transition metal oxide, and thereby it is possible for the electrode material to suitably adhere to the vibration film 412.

The second lower electrode 415 corresponds to a third electrode and is provided at a position at which the second lower electrode overlaps the piezoelectric film 416 on the surface of the flexible film 412A on the +Z side in the plan view (refer to FIG. 5). The second lower electrode 415 is formed of the same material as that of the first lower electrode 414 and has a substantially mirror-symmetric relationship with the first lower electrode 414 with respect to a virtual line L parallel to the Y direction through the center of the piezoelectric film 416. An end surface 415C of the second lower electrode 415 on a −X side is separated from the end surface 414C of the first lower electrode 414 by the gap G1 having the predetermined dimension in the X direction. The second lower electrode 415 is connected to a second lower electrode 415 of an adjacent ultrasonic transducer 45 in the Y direction, with the second lower electrode line 415A.

In addition, the first lower electrode 414 and the second lower electrode 415 are separated from each other with the piezoelectric film 416 therebetween in the plan view and are insulated from each other. In other words, the first lower electrode 414 and the second lower electrode 415 are separated from each other with the piezoelectric film 416 between the first lower electrode 414 and the second lower electrode 415 in the plan view and are insulated from each other.

The piezoelectric film 416 corresponds to a piezoelectric body, is positioned in the opening 411A in the plan view, and is laminated on any one of the first lower electrode 414, the second lower electrode 415, and the flexible film 412A. For example, the piezoelectric film 416 is formed of a transition metal oxide having a perovskite structure, more specifically, lead zirconate titanate (PTZ) containing lead (Pb), titanium (Ti), and zirconium (Zr). The piezoelectric film 416 is formed to have a composition ratio of 52:48 between Zr and Ti. A film of PZT is formed to have the composition ratio, and thereby it is possible to form the piezoelectric film 416 having a good piezoelectric property, that is, a high piezoelectric constant (e constant).

The first upper electrode 417 corresponds to a second electrode and is provided on the +Z side of the piezoelectric film 416. In addition, the first upper electrode 417 is provided at a position at which the first upper electrode overlaps the first lower electrode 414 in the plan view. In other words, the first lower electrode 414 and the first upper electrode 417 are separated from each other by a gap G2 having a predetermined dimension via the piezoelectric film 416 and overlap each other in the plan view. In other words, the first lower electrode 414 and the first upper electrode 417 are separated from each other by the gap G2 having the predetermined dimension with the piezoelectric film 416 between the first lower electrode 414 and the first upper electrode 417 and overlap each other in the plan view. In the embodiment, the first upper electrode 417 has a substantially rectangular planar shape as shown in FIG. 5, and an end surface 417C on the +X side is separated from the second upper electrode 418 by the gap G1 having the predetermined dimension in the X direction. The first upper electrode 417 is formed by the same electrode material as that of the first lower electrode 414.

The first upper electrode 417 is connected to the first upper electrode pad 417P and a first upper electrode 417 of an adjacent ultrasonic transducer 45 in the Y direction, with the first upper connection electrode 417A and the first upper leading line 417B.

The second upper electrode 418 corresponds to a fourth electrode and is provided on the +Z side of the piezoelectric film 416. In addition, the second upper electrode 418 is provided at a position at which the second upper electrode overlaps at least a part of the second lower electrode 415 in the plan view. In other words, the second lower electrode 415 and the second upper electrode 418 are separated by the gap G2 having the predetermined dimension via the piezoelectric film 416 and overlap each other in the plan view. In other words, the second lower electrode 415 and the second upper electrode 418 are separated from each other by the gap G2 having the predetermined dimension with the piezoelectric film 416 between the second lower electrode 415 and the second upper electrode 418 and overlap each other in the plan view. In the embodiment, the second upper electrode 418 has a substantially rectangular planar shape as shown in FIG. 5, and an end surface 418C on the +X side is separated from the end surface 417C of the first upper electrode 417 by the gap G1 having the predetermined dimension in the X direction. The second upper electrode 418 is formed by the same electrode material as that of the first lower electrode 414.

The second upper electrode 418 is connected to the second upper electrode pad 418P and a second upper electrode 418 of an adjacent ultrasonic transducer 45 in the Y direction, with the second upper connection electrode 418A the second upper leading line 418B.

In addition, the first upper electrode 417 and the second upper electrode 418 are separated from each other in the plan view and are insulated from each other.

In the embodiment, a distance between the first lower electrode 414 and the second upper electrode 418 is longer than the dimension (distance) of the gap G1 between the end surface 415C of the second lower electrode 415 on the −X side and the end surface 414C of the first lower electrode 414. In addition, the distance between the first lower electrode 414 and the second upper electrode 418 is longer than the dimension (distance) of the gap G2 between the first lower electrode 414 and the first upper electrode 417.

More preferably, the distances satisfy the conditions described above, and the end surface 414C of the first lower electrode 414 overlaps the end surface 417C of the first upper electrode 417 in the plan view. An overlap between the end surface 414C and the end surface 417C means that it is possible to allow a manufacturing error as long as the configuration satisfies the conditions described above.

When such a configuration is used, there can be less concern that an unintended short circuit between the electrodes (for example, a short circuit between the first lower electrode 414 and the second upper electrode 418) will occur.

In addition, in the embodiment, a distance between the second lower electrode 415 and the first upper electrode 417 is longer than the dimension (distance) of the gap G1 between the end surface 415C of the second lower electrode 415 on the −X side and the end surface 414C of the first lower electrode 414. In addition, the distance between the second lower electrode 415 and the first upper electrode 417 is longer than the dimension (distance) of the gap G2 between the second lower electrode 415 and the second upper electrode 418.

More preferably, the distances satisfy the conditions described above, and the end surface 415C of the second lower electrode 415 overlaps the end surface 418C of the second upper electrode 418 in the plan view. An overlap between the end surface 415C and the end surface 418C means that it is possible to allow a manufacturing error as long as the configuration satisfies the conditions described above.

When such a configuration is used, there can be less concern that an unintended short circuit between the electrodes (for example, a short circuit between the second lower electrode 415 and the first upper electrode 417) will occur.

In the ultrasonic transducer 45 described above, in a case where the ultrasonic wave is transmitted, voltages are applied between the first lower electrode 414 and the first upper electrode 417 and between the second lower electrode 415 and the second upper electrode 418 in a state of the short circuit between the first lower electrode 414 and the second lower electrode 415 and between the first upper electrode 417 and the second upper electrode 418.

In addition, in the ultrasonic transducer 45, in a case where the ultrasonic wave is received, electric signals due to potential differences produced between the first lower electrode 414 and the second lower electrode 415 and between the first upper electrode 417 and the second upper electrode 418 in a state of the short circuit between the first lower electrode 414 and the first upper electrode 417 and between the second lower electrode 415 and the second upper electrode 418.

Configuration of Circuit Substrate

The circuit substrate 23 is provided as a driver circuit for controlling the ultrasonic transducers 45, and the ultrasonic device 22 is bonded to the circuit substrate via a wiring member (not shown) such as flexible printed circuits (FPC). As shown in FIG. 2, the circuit substrate 23 is configured to have a switch circuit 231, a selection circuit 232, a transmitting circuit 233, a receiving circuit 234, and a polarization circuit 235.

Configuration of Selection Circuit, Transmitting Circuit, and Receiving Circuit

The selection circuit 232 is connected to the ultrasonic sensor 24 via the switch circuit 231 and switches connection between a transmitting connection by which the ultrasonic sensor 24 and the transmitting circuit 233 are connected to each other and the receiving connection in which the ultrasonic sensor 24 and the receiving circuit 234 are connected to each other, based on the control of the control device 10.

When the connection is switched to the transmitting connection in accordance with the control of the control device 10, the transmitting circuit 233 outputs a transmitting signal indicating that the ultrasonic wave is transmitted to the ultrasonic sensor 24 via the selection circuit 232.

When the connection is switched to the receiving connection in accordance with the control of the control device 10, the receiving circuit 234 outputs a receiving signal input from the ultrasonic sensor 24 via the selection circuit 232, to the control device 10. For example, the receiving circuit 234 is configured to have a low noise amplifier circuit, a voltage control attenuator, a programmable gain amplifier, a low pass filter, an A/D converter, or the like, converts the receiving signal into a digital signal, removes a noise component, executes various types of signal processing such as amplification to a predetermined signal level, and then outputs the processed receiving signal to the control device 10.

Configuration of Switch Circuit

The switch circuit 231 corresponds to a switching unit and is connected to the respective electrode pads 414P, 415P, 417P, and 418P of the plurality of ultrasonic transducer groups 45A. The switch circuit 231 is configured to be capable of switching between a first connection state that is selected when the ultrasonic wave is transmitted and a second connection state that is selected when the ultrasonic wave is received in the ultrasonic transducer groups 45A based on the control of the control device 10.

Specifically, in the first connection state, the switch circuit 231 is connected to the first lower electrode pad 414P and the second lower electrode pad 415P and is connected to the first upper electrode pad 417P and the second upper electrode pad 418P. In addition, in the second connection state, the switch circuit 231 is connected to the first lower electrode pad 414P and the first upper electrode pad 417P and is connected to the second lower electrode pad 415P and the second upper electrode pad 418P.

First Connection State when Ultrasonic Wave is Transmitted

Figure 7:
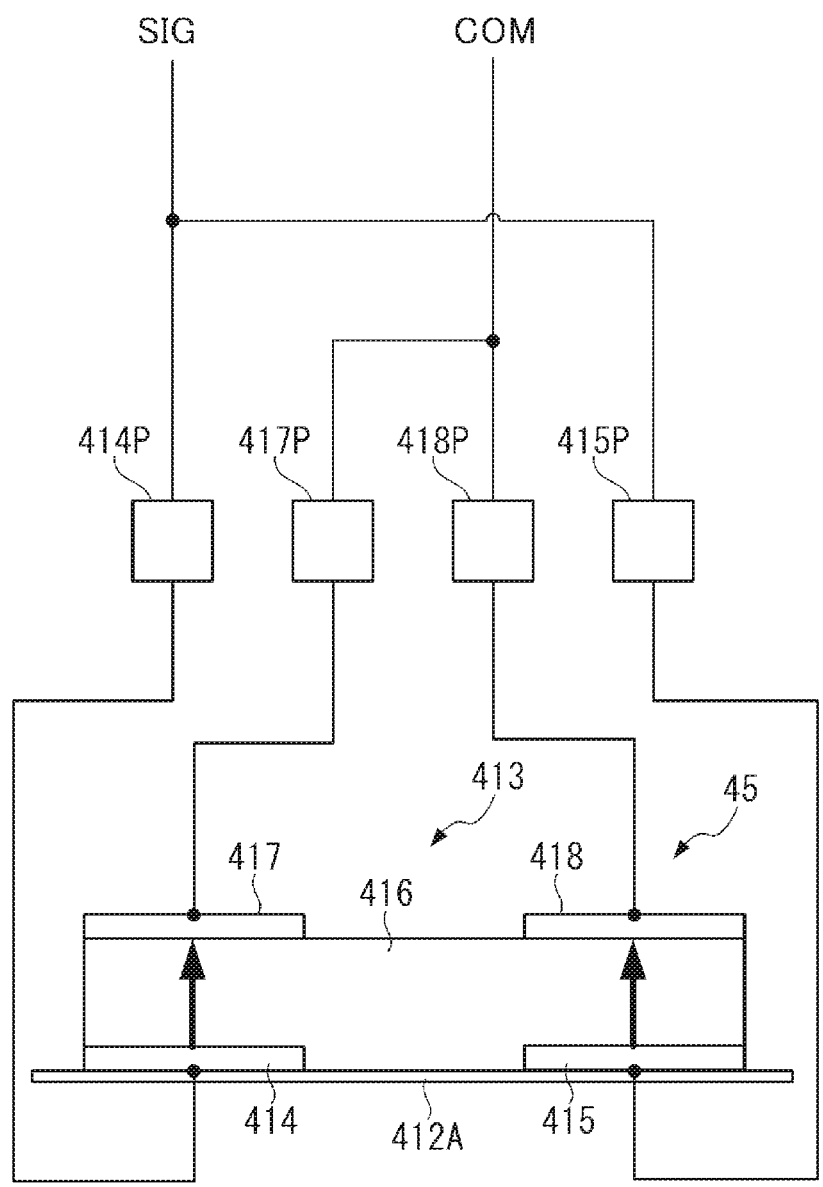
FIG. 7 is a diagram schematically showing a first connection state in the first embodiment.

FIG. 7 is a diagram schematically showing a connection state of the electrodes 414, 415, 417, and 418 of the ultrasonic transducer 45 in the first connection state.

The switch circuit 231 switches the connection state to the first connection state shown in FIG. 7 based on the control of the control device 10 when the ultrasonic wave is transmitted. In the first connection state, the switch circuit 231 is connected to the first lower electrode pad 414P and the second lower electrode pad 415P and is connected to the first upper electrode pad 417P and the second upper electrode pad 418P. In this manner, the first lower electrode 414 and the second lower electrode 415 of the ultrasonic transducer 45 are short-circuited and the first upper electrode 417 and the second upper electrode 418 thereof are short-circuited.

In the embodiment, the second upper electrode pads 418P of the ultrasonic transducer groups 45A are connected to a ground circuit or the like, for example, and are set to have a predetermined common potential (for example, a zero potential). In other words, the second upper electrode 418 functions as a common electrode (COM electrode) set to the common potential regardless of the connection state.

In addition, the first lower electrode pads 414P of the ultrasonic transducer groups 45A are connected to the selection circuit 232 via the switch circuit 231, receives a transmitting signal input from the transmitting circuit 233 when the ultrasonic wave is transmitted, and outputs a receiving signal to the receiving circuit 234 when the ultrasonic wave is received. In other words, the first lower electrode 414 functions as a signal electrode (SIG electrode) for inputting the transmitting signal or outputting a receiving signal regardless of the connection state.

In the first connection state shown in FIG. 7, the first upper electrode 417 and the second upper electrode 418 function as the COM electrodes, and the first lower electrode 414 and the second lower electrode 415 function as the SIG electrodes. In other words, a rectangular voltage having a predetermined frequency is applied to the first lower electrode 414 and the second lower electrode 415, and thereby potential differences are produced between the first lower electrode 414 and the first upper electrode 417 and between the second lower electrode 415 and the second upper electrode 418, and the piezoelectric film 416 expands and contracts in an in-plane direction. There is a difference in an amount of expansion/contraction on a side of the flexible film 412A and an opposite side of the piezoelectric film 416, and the piezoelectric film 416 is displaced in its thickness direction and vibrates due to the difference. The flexible film 412A vibrates due to the vibration of the piezoelectric film 416, and the ultrasonic wave is transmitted.

Second Connection State when Ultrasonic Wave is Received

Figure 8:
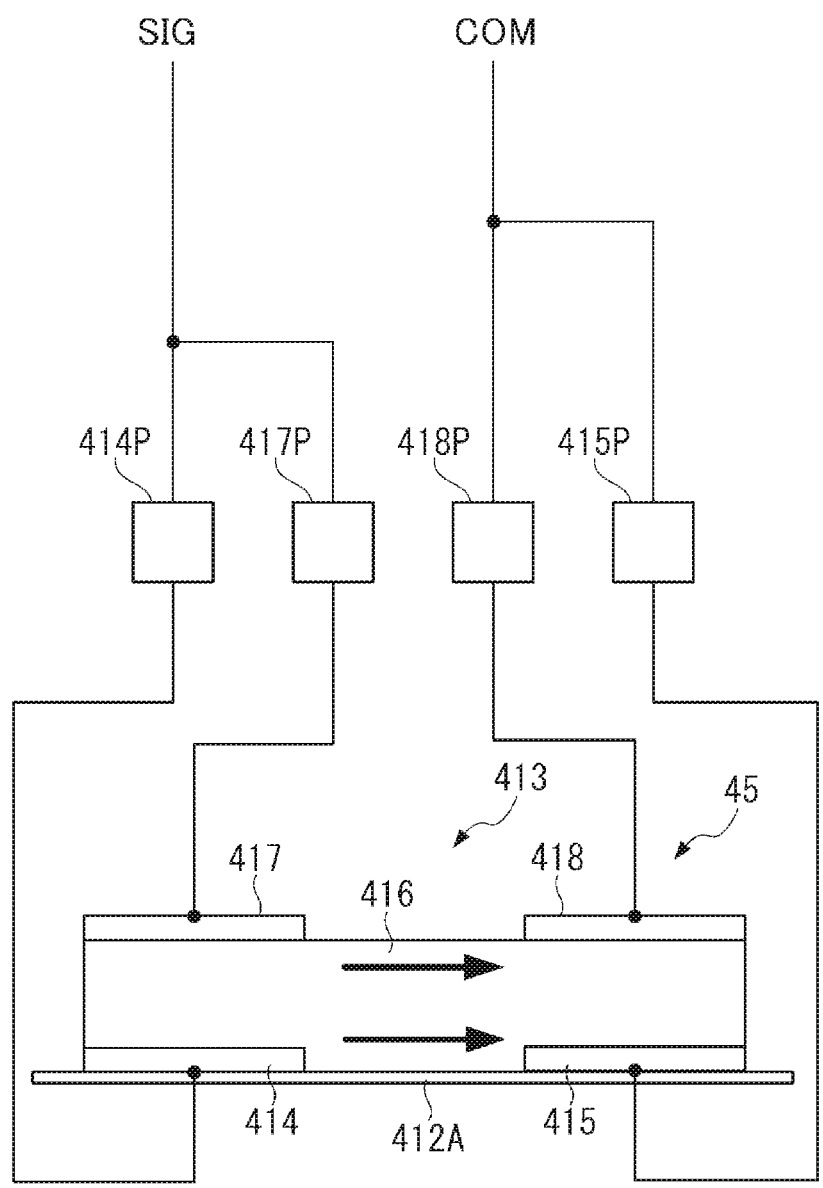
FIG. 8 is a diagram schematically showing a second connection state in the first embodiment.

FIG. 8 is a diagram schematically showing a connection state of the electrodes 414, 415, 417, and 418 of the ultrasonic transducer 45 in the second connection state.

The switch circuit 231 switches the connection state to the second connection state shown in FIG. 8 based on the control of the control device 10 when the ultrasonic wave is received. In the second connection state, the switch circuit 231 is connected to the first lower electrode pad 414P and the first upper electrode pad 417P and is connected to the second lower electrode pad 415P and the second upper electrode pad 418P. In this manner, the first lower electrode 414 and the first upper electrode 417 of the ultrasonic transducer 45 are short-circuited and the second lower electrode 415 and the second upper electrode 418 thereof are short-circuited.

In the second connection state shown in FIG. 8, the second lower electrode 415 and the second upper electrode 418 function as the COM electrodes, and the first lower electrode 414 and the first upper electrode 417 function as the SIG electrodes. In other words, when the flexible film 412A vibrates due to the ultrasonic wave, a potential difference is produced in the piezoelectric film 416 according to the vibration, and potential differences are produced between the first lower electrode 414 and the second lower electrode 415 and between the first upper electrode 417 and the second upper electrode 418. The electric signals output from the first lower electrode 414 and the first upper electrode 417 according to the potential differences are input to the control device 10 via the receiving circuit 234, and thereby the ultrasonic wave is detected.

Here, in the second connection state shown in FIG. 8, the capacitor configured between the first lower electrode 414 and the first upper electrode 417 and the capacitor configured between the second lower electrode 415 and the second upper electrode 418 are connected in parallel. Therefore, an electric signal corresponding to a sum of the potential difference between the first lower electrode 414 and the first upper electrode 417 and the potential difference between the second lower electrode 415 and the second upper electrode 418 is output from the ultrasonic transducer 45, and the detection sensitivity of the ultrasonic wave of the ultrasonic transducer 45 is improved.

The ultrasonic transducers 45 of the ultrasonic transducer group 45A are connected in parallel. Therefore, an electric signal corresponding to the sum of the potential differences produced in the capacitors of the ultrasonic transducers 45 is output from the ultrasonic transducer group 45A, and the detection sensitivity of the ultrasonic transducer group 45A is improved.

Configuration of Polarization Circuit

The polarization circuit 235 applies a voltage between the COM electrode and the SIG electrode based on the control of a polarization control unit 142 and performs a polarization process of the piezoelectric film 416 of the piezoelectric element 413.

Specifically, the polarization circuit 235 performs a first polarization process of causing a polarization state of the piezoelectric film 416 to become a state suitable for transmitting the ultrasonic wave, before the ultrasonic wave is transmitted. In the first polarization process, in the first connection state shown in FIG. 7, the polarization circuit 235 applies first polarization voltages between the first lower electrode 414 and the first upper electrode 417 and between the second lower electrode 415 and the second upper electrode 418 and performs the polarization process of the piezoelectric film 416.

In addition, the polarization circuit 235 performs a second polarization process of causing the polarization state of the piezoelectric film 416 to become a state suitable for receiving the ultrasonic wave, before the ultrasonic wave is received. In the second polarization process, in the second connection state shown in FIG. 8, the polarization circuit 235 applies second polarization voltages between the first lower electrode 414 and the second lower electrode 415 and between the first upper electrode 417 and the second upper electrode 418 and performs the polarization process of the piezoelectric film 416.

Configuration of Control Device

As shown in FIG. 2, the control device 10 is configured to include an operating unit 11, a display unit 12, a storage unit 13, and a controller 14. For example, the control device 10 may use a terminal device such as a tablet terminal, a smart phone, or a personal computer, and may be a dedicated terminal device for operating the ultrasonic probe 2.

The operating unit 11 is a user interface (UI) through which a user operates the ultrasonic apparatus 1, and can be configured of a touch panel, an operating button, a keyboard, a mouse, or the like which are provided on the display unit 12.

For example, the display unit 12 is configured of a liquid crystal display or the like, and displays an image.

The storage unit 13 stores various types of programs or various types of data for controlling the ultrasonic apparatus 1.

For example, the controller 14 is configured to have an arithmetic circuit such as a central processing unit (CPU), and the storage circuit such as a memory. The controller 14 performs reading of the various types of programs stored in the storage unit 13, thereby functioning as a switching control unit 141, a polarization control unit 142, and a transmitting/receiving control unit 143 and controlling the ultrasonic sensor 24.

The switching control unit 141 controls the switch circuit 231, switches the connection state to the first connection state when the ultrasonic wave is transmitted, and switches the connection state to the second connection state when the ultrasonic wave is received.

The polarization control unit 142 controls the selection circuit 232 and the polarization circuit 235 and performs the polarization process of the piezoelectric film 416. In other words, the polarization control unit 142 controls the selection circuit 232 and is connected to the switch circuit 231 and the polarization circuit 235. In addition, the polarization control unit 142 controls the polarization circuit 235, performs the first polarization process before the ultrasonic wave is transmitted, and performs the second polarization process before the reception of the ultrasonic wave is received.

The transmitting/receiving control unit 143 controls the transmission and the reception of the ultrasonic wave. For example, the transmitting/receiving control unit 143 controls the selection circuit 232, is connected to the switch circuit 231 and the transmitting circuit 233 when the ultrasonic wave is transmitted, and is connected to the switch circuit 231 and the receiving circuit 234 when the ultrasonic wave is received. In addition, the transmitting/receiving control unit 143 controls generation and output processes of the transmitting signal with respect to the transmitting circuit 233 and controls frequency setting or gain setting of the receiving signal with respect to the receiving circuit 234.

Ultrasonic Measuring Process in Ultrasonic Apparatus

Figure 9:
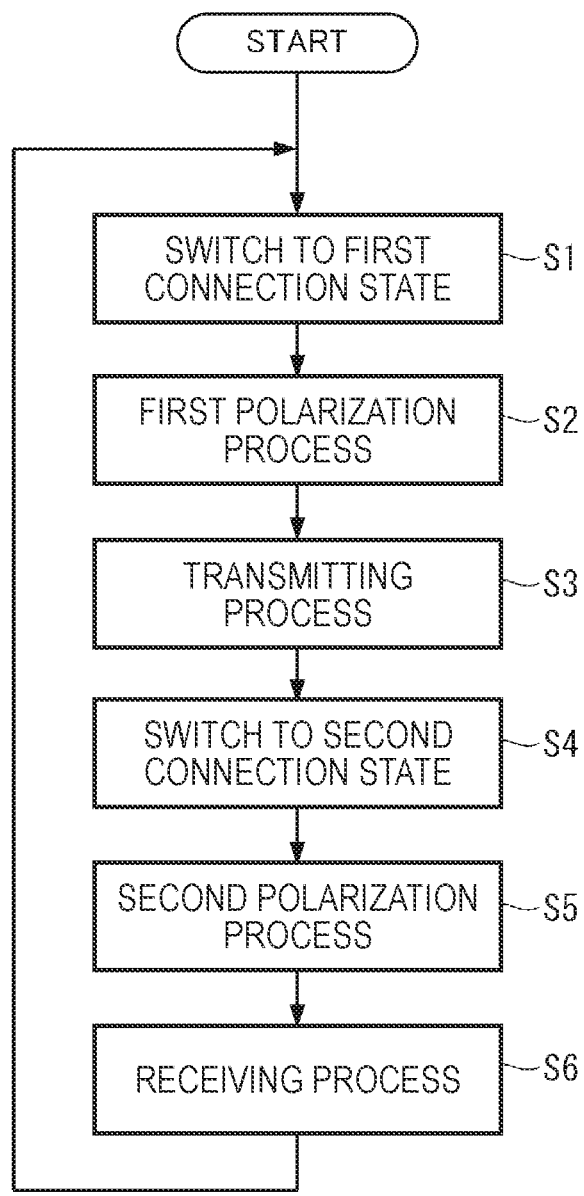
FIG. 9 is a flowchart showing an example of an ultrasonic measuring process in the first embodiment.

FIG. 9 is a flowchart showing an example of an ultrasonic measuring process in the ultrasonic apparatus 1.

The controller 14 starts the ultrasonic measuring process when a measuring start instruction such as an input operation is received by the operating unit 11.

First, the switching control unit 141 controls the switch circuit 231 and switches the connection state to the first connection state (refer to FIG. 7) (Step S1).

In the first connection state, the first lower electrode pad 414P and the second lower electrode pad 415P are short-circuited and the first upper electrode pad 417P and the second upper electrode pad 418P are short-circuited.

Next, the polarization control unit 142 controls the selection circuit 232 and the polarization circuit 235 and performs the first polarization process (Step S2).

The polarization control unit 142 controls the selection circuit 232 and is connected to the switch circuit 231 and the polarization circuit 235. In addition, the polarization control unit 142 controls the polarization circuit 235, applies the first polarization voltages between the first lower electrode 414 and the first upper electrode 417 and between the second lower electrode 415 and the second upper electrode 418, and performs the polarization process of the piezoelectric film 416.

Next, the transmitting/receiving control unit 143 performs a transmitting process of the ultrasonic wave (Step S3).

The transmitting/receiving control unit 143 controls the selection circuit 232 and is connected to the switch circuit 231 and the transmitting circuit 233. The transmitting/receiving control unit 143 controls the generation and output processes of the transmitting signal with respect to the transmitting circuit 233. In the ultrasonic transducer 45 to which the transmitting signal has been input, the piezoelectric film 416 vibrates due to the potential differences produced between the first lower electrode 414 and the first upper electrode 417 and between the second lower electrode 415 and the second upper electrode 418, the flexible film 412A vibrates due to the vibration of the piezoelectric film 416, and the ultrasonic wave is detected.

First, the switching control unit 141 controls the switch circuit 231 and switches the connection state to the second connection state (refer to FIG. 8) (Step S4). In the second connection state, the first lower electrode 414 and the first upper electrode 417 of the ultrasonic transducer 45 are short-circuited and the second lower electrode 415 and the second upper electrode 418 thereof are short-circuited.

Next, the polarization control unit 142 controls the selection circuit 232 and the polarization circuit 235 and performs the second polarization process (Step S5).

The polarization control unit 142 controls the selection circuit 232 and is connected to the switch circuit 231 and the polarization circuit 235. In addition, the polarization control unit 142 applies the second polarization voltages between the first lower electrode 414 and the second lower electrode 415 and between the first upper electrode 417 and the second upper electrode 418 and performs the polarization process of the piezoelectric film 416.

Here, in the embodiment, in order to have a larger dimension of the gap G2 (refer to FIG. 6) between the first lower electrode 414 and the first upper electrode 417 than the dimension of the gap G1 between the first lower electrode 414 and the second lower electrode 415 (the first upper electrode 417 and the second upper electrode 418) and to sufficiently increase the piezoelectric property of the piezoelectric film 416, the second polarization voltage needs to be higher than the first polarization voltage. The second polarization voltage is set to apply an electric field of 10 kV/cm or higher between the first lower electrode 414 and the second lower electrode 415 (the first upper electrode 417 and the second upper electrode 418) of the ultrasonic transducer 45.

In the embodiment, a distance between the first lower electrode 414 and the second lower electrode 415 (the first upper electrode 417 and the second upper electrode 418) is 6 μm, for example, and 30 V is applied therebetween as the second polarization voltage. Hence, an electric field of 500 kV/cm is applied to the piezoelectric films 416 of the ultrasonic transducers 45.

Next, the transmitting/receiving control unit 143 performs a receiving process of the ultrasonic wave (Step S6).

The transmitting/receiving control unit 143 controls the selection circuit 232 and is connected to the switch circuit 231 and the receiving circuit 234. As described above, the electric signal in response to the potential differences produced between the first lower electrode 414 and the second lower electrode 415 and between the first upper electrode 417 and the second upper electrode 418 due to the vibration of the flexible film 412A and the vibration of the piezoelectric film 416 by the ultrasonic wave is output to the receiving circuit 234 from the ultrasonic transducer 45 (ultrasonic transducer group 45A). The receiving circuit 234 performs various types of processing on the receiving signal and the outputs the processed signal to the control device 10. In this manner, the ultrasonic wave is detected by using the ultrasonic transducer 45.

The controller 14 of the control device 10 acquires an internal tomographic image based on the detection result of the ultrasonic wave or measures a state (for example, bloodstream or the like) of the organ in the living body. The ultrasonic apparatus 1 configured as described above executes Step S1 to Step S6 repeatedly until an end instruction of the measurement process is received.

Operational Effect of First Embodiment

The ultrasonic transducer 45 of the embodiment includes the piezoelectric element 413, and the piezoelectric element includes the piezoelectric film 416 and the first lower electrode 414, the second lower electrode 415, the first upper electrode 417, and the second upper electrode 418 that are in contact with the piezoelectric film 416. Of the electrodes, the first lower electrode 414 and the first upper electrode 417 are separated from each other via the piezoelectric film 416 (interposed therebetween) and overlap each other in the plan view when viewed in the thickness direction of the piezoelectric film 416. In addition, the second lower electrode 415 and the second upper electrode 418 are separated via the piezoelectric film 416 (interposed therebetween) and overlap each other in the plan view. In addition, the first lower electrode 414 and the second lower electrode 415 are separated from each other and the first upper electrode 417 and the second upper electrode 418 are separated from each other in the X direction.

In the ultrasonic transducer 45 configured as described above, while it is possible to decrease the distance (that is, the gap G2) between the first lower electrode 414 and the first upper electrode 417 (the second lower electrode 415 and the second upper electrode 418), it is possible to increase the distance (that is, the gap G1) between the first lower electrode 414 and the second lower electrode 415 (the first upper electrode 417 and the second upper electrode 418). In this manner, it is possible to improve the transmission output and receiving sensitivity of the ultrasonic transducer 45 at the same time.

In other words, when the ultrasonic wave is transmitted by using the ultrasonic transducer 45, the switch circuit 231 of the circuit substrate 23 switches the connection state to the first connection state that is selected when the electrode connection states are transmitted, the voltages are applied between the first lower electrode 414 and the first upper electrode 417 and between the second lower electrode 415 and the second upper electrode 418, and thereby the electric field in the thickness direction of the piezoelectric film 416 is applied to the piezoelectric film 416. Here, a strain amount of the piezoelectric film 416 is inversely proportional to the distances between the electrodes, with respect to the applied voltage between the electrodes. Therefore, the distance (the gap G2) between the first lower electrode 414 and the first upper electrode 417 (the second lower electrode 415 and the second upper electrode 418) is decreased, and thereby it is possible to increase the transmission output of the ultrasonic transducer 45.

On the other hand, when the ultrasonic wave is received, the switch circuit 231 of the circuit substrate 23 switches the connection state to the second connection state that is selected when the electrode connection states are received, the potential difference produced between the first lower electrode 414 and the second lower electrode 415 (the potential difference produced between the first upper electrode 417 and the second upper electrode 418) due to the strain of the piezoelectric film 416 is output as the electric signal. Here, the potential difference between the electrodes is proportional to the distance between the electrodes, with respect to the strain of the piezoelectric body. Therefore, the distance (the gap G1) between the first lower electrode 414 and the second lower electrode 415 (the first upper electrode 417 and the second upper electrode 418) is increased, and thereby it is possible to increase the receiving sensitivity of the ultrasonic transducer 45.

As described above, in the ultrasonic transducer 45 of the embodiment, it is possible to increase the transmission output by decreasing the gap G2, and it is possible to increase the receiving sensitivity by increasing the gap G1.

In the first connection state, the end surface 414C of the first lower electrode 414, to which the voltage is applied, and the end surface 417C of the first upper electrode 417 overlap each other in the plan view when viewed in the thickness direction (Z direction) of the piezoelectric film 416. In such a configuration, it is possible to increase an amount of an overlap between the first lower electrode 414 and the first upper electrode 417, and it is possible to efficiently apply the voltage to the piezoelectric film 416. In addition, similarly, the end surface 415C of the second lower electrode 415 and the end surface 418C of the second upper electrode 418 overlap each other in the plan view, and thus it is possible to efficiently apply the voltage to the piezoelectric film 416 that is positioned between the second lower electrode 415 and the second upper electrode 418. Hence, it is possible to improve the transmission output of the ultrasonic transducer 45.

In addition, in the second connection state, it is possible to easily perform the impedance matching between the ultrasonic transducer 45 and an external circuit (for example, circuits configured of the circuit substrate 23) that is connected to the ultrasonic transducer 45. In other words, in the second connection state, the capacitor formed by the first lower electrode 414 and the second lower electrode 415 and the capacitor formed by the first upper electrode 417 and the second upper electrode 418 are connected in parallel. In such a configuration, it is possible to increase the capacitance of the ultrasonic transducer 45. In this manner, it is possible to suppress an influence of stray capacitance of the external circuit such as the circuit substrate 23, and thus it is possible to easily perform the impedance matching with the external circuit. Hence, it is possible to suppress a loss of the receiving signal that is output from the ultrasonic transducer 45, and it is possible to improve the detection accuracy or the receiving sensitivity of the ultrasonic wave.

In addition, the distance between the first lower electrode 414 and the second lower electrode 415 constituting the capacitor in the second connection state is the same as the distance between the first upper electrode 417 and the second upper electrode 418 constituting the capacitor. In such a configuration, when the ultrasonic wave is received, it is possible to suppress the concentration of electric charge to the capacitor on the side on which the distance dimension between the electrodes is shorter, and it is possible to cause the capacitor to uniformly function. Hence, it is possible to more reliably increase the capacitance of the ultrasonic transducer 45.

In addition, the first lower electrode 414 and the second lower electrode 415 which constitute the capacitor in the second connection state are separated from each other with the central portion of the piezoelectric film 416 therebetween in the X direction. Here, when the ultrasonic wave is received, the first lower electrode 414 and the second lower electrode 415 are disposed such that the central portion of the piezoelectric film 416, at which the strain is higher than an outer circumferential portion, is interposed therebetween. Therefore, when the ultrasonic wave is received, it is possible to increase the potential difference between the first lower electrode 414 and the second lower electrode 415, and it is possible to improve the receiving sensitivity of the ultrasonic wave. In addition, the same is true of the first upper electrode 417 and the second upper electrode 418.

The distance between the first lower electrode 414 and the second upper electrode 418 is longer than the dimension of the gap G1 between the first lower electrode 414 and the second lower electrode 415 or the gap G2 between the first lower electrode 414 and the first upper electrode 417. In this manner, it is possible to suppress the short circuit between the first lower electrode 414 and the second upper electrode 418. In addition, similarly, the distance between the second lower electrode 415 and the first upper electrode 417 is longer than the dimension of the gap G1 and the gap G2, and thus it is possible to suppress the short circuit between the second lower electrode 415 and the first upper electrode 417.

In addition, the embodiment employs a configuration in which the switch circuit 231 can switch the connection state of the electrodes of the ultrasonic transducer 45 between the first connection state and the second connection state. In such a configuration, when the ultrasonic transducer 45 is driven, the switching control unit 141 controls the switch circuit 231 and switches the connection state between the first connection state and the second connection state, and thereby it is possible to appropriately set the connection state of the electrodes when the ultrasonic wave is transmitted and is received.

In addition, the switch circuit 231 is provided, and thereby it is possible to reduce a processing load of the controller 14. For example, in the embodiment, when the ultrasonic wave is transmitted, the switching control unit 141 controls the switch circuit 231 and switches the connection state to the first connection state. In this manner, the transmitting/receiving control unit 143 may control the transmitting circuit 233 such that a common drive signal is output from the lower electrodes 414 and 415, which are the SIG electrodes, and the processing load is reduced, compared to a case where it is necessary to individually drive the lower electrodes 414 and 415. In addition, also when the ultrasonic wave is received, there is no need to individually detects signals which are output from the first lower electrode 414 and the first upper electrode 417, which are the SIG electrodes, and the processing load is reduced.

Further, it is possible to reduce the number of signals which are input to and output from the switch circuit 231, and it is possible to simplify the configurations of the selection circuit 232, the transmitting circuit 233, and the receiving circuit 234.

In the embodiment, the polarization circuit 235 that applies the polarization voltage to the piezoelectric film 416 is provided. The polarization control unit 142 controls the polarization circuit 235, the switch circuit 231 switches the connection state to the first connection state, and then the first polarization process is executed before the ultrasonic wave is transmitted. In the first polarization process, the polarization control unit 142 applies an electric field in the thickness direction to the piezoelectric film 416 disposed between the first lower electrode 414 and the first upper electrode 417 and between the second lower electrode 415 and the second upper electrode 418. In this manner, it is possible to cause the polarization state of the piezoelectric film 416 to become the state suitable for transmitting the ultrasonic wave. The first polarization process is executed before the ultrasonic wave is transmitted, and thereby it is possible to more improve the transmission output of the ultrasonic transducer 45, and thus it is possible to more improve the accuracy of ultrasonic measurement in the ultrasonic apparatus 1.

In addition, the polarization control unit 142 controls the polarization circuit 235, the switch circuit 231 switches the connection state to the second connection state, and then the second polarization process is executed before the ultrasonic wave is received. In the second polarization process, in the plan view when viewed from the thickness direction of the piezoelectric film 416, the electric field is applied in the direction (X direction) orthogonal to the thickness direction with respect to the piezoelectric film 416 disposed between the first lower electrode 414 and the second lower electrode 415 and between the first upper electrode 417 and the second upper electrode 418. In this manner, it is possible to cause the polarization state of the piezoelectric film 416 to become the state suitable for transmitting the ultrasonic wave. The second polarization process is executed before the ultrasonic wave is received, and thereby it is possible to more improve the receiving sensitivity of the ultrasonic transducer 45, and thus it is possible to more improve the accuracy of ultrasonic measurement in the ultrasonic apparatus 1.

In the embodiment, the ultrasonic array AL is configured of the plurality of ultrasonic transducers 45. As described above, the ultrasonic transducer 45 is capable of improving the transmitting sensitivity and receiving sensitivity of the ultrasonic wave and, thus, is suitable for being used for the transmission and reception of the ultrasonic wave. Hence, it is possible to more increase the number of both of transmitting and receiving ultrasonic transducers per unit area, and thus it is possible to improve the transmission output and the receiving sensitivity of the ultrasonic wave, compared to an ultrasonic array including a transmitting-dedicated ultrasonic transducer and a receiving-dedicated ultrasonic transducer.

In addition, the ultrasonic array AL includes a plurality of ultrasonic transducer groups 45A constituting one transmitting/receiving channel configured to have a plurality of ultrasonic transducers 45 which are disposed in the Y direction and are connected to each other. In the ultrasonic transducer group 45A, in the second connection state, the capacitors, which are formed by the first lower electrodes 414 and the second lower electrodes 415 of the ultrasonic transducers 45, are connected in parallel. In addition, the capacitors, which are formed by the first upper electrodes 417 and the second upper electrodes 418 are connected in parallel. Hence, it is possible to increase the capacitance of one transmitting/receiving channel in the second connection state, and it is possible to easily perform the impedance matching with the external circuit, compared to a case where one transmitting/receiving channel is configured of one ultrasonic transducer 45.

Second Embodiment

Next, a second embodiment will be described.

In the first embodiment described above, in the ultrasonic transducer 45, the first lower electrode 414 and the second lower electrode 415 are disposed on the flexible film 412A, and the first upper electrode 417 and the second upper electrode 418 are disposed to be opposite to each other on the piezoelectric film 416. By comparison, the second embodiment differs from the first embodiment in that a third lower electrode is disposed between the first lower electrode 414 and the second lower electrode 415, and a third upper electrode is disposed between the first upper electrode 417 and the second upper electrode 418.

Hereinafter, the receiving transducer according to the embodiment will be described. In the following description, the same reference signs are assigned to the same configurations as those of the first embodiment, and thus the description thereof is omitted or simplified.

Figure 10:
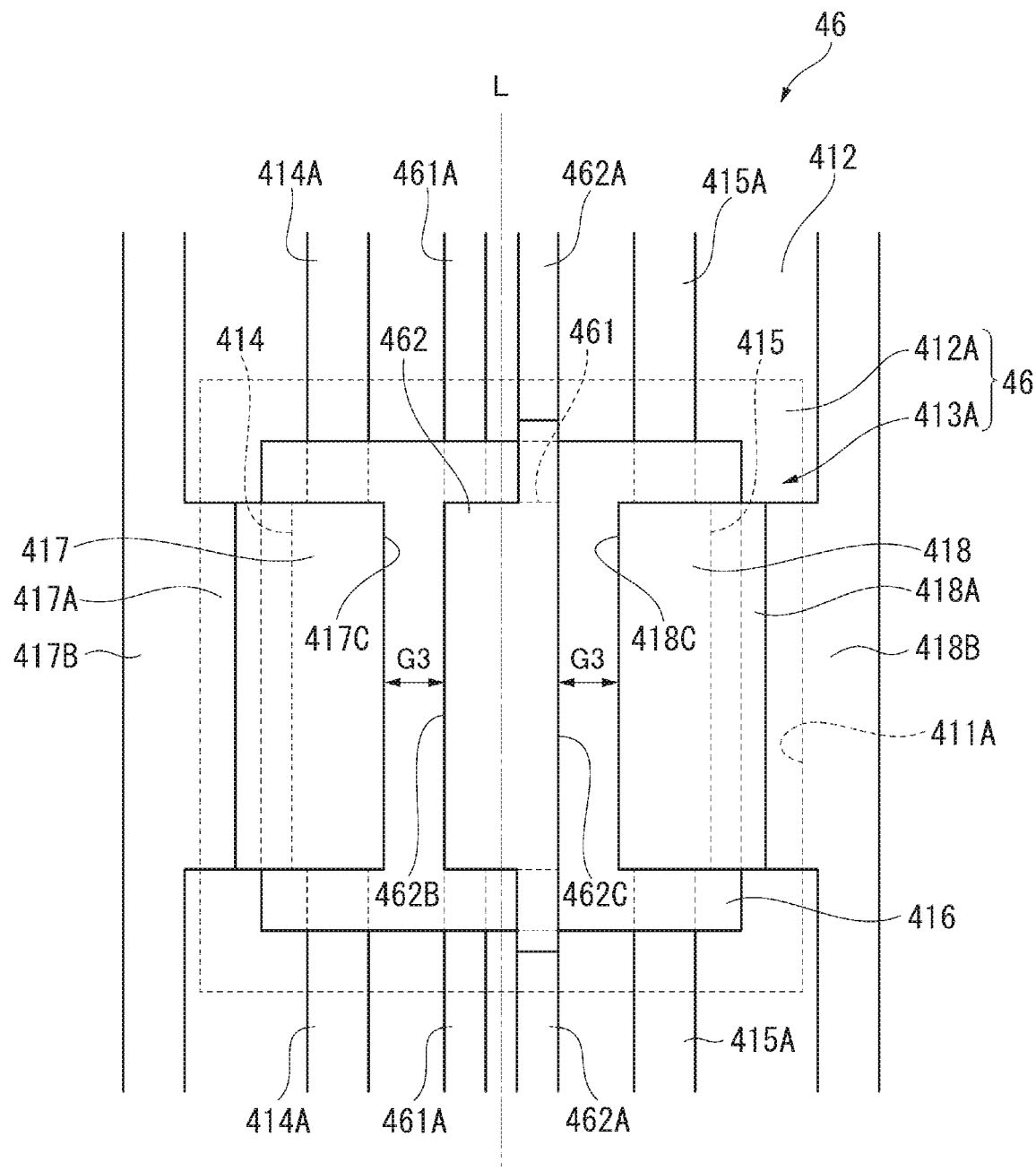
FIG. 10 is a plan view showing a schematic configuration of an ultrasonic transducer of a second embodiment.
Figure 11:
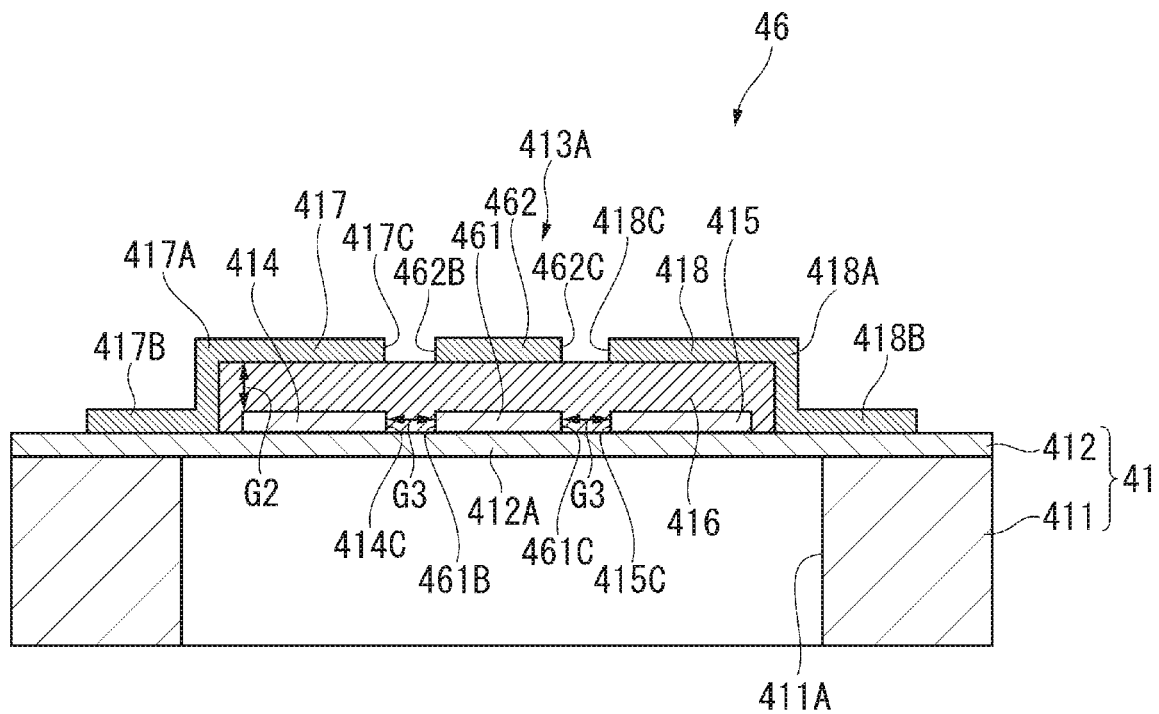
FIG. 11 is a sectional view showing a schematic configuration of the ultrasonic transducer of the second embodiment.
Figure 12:
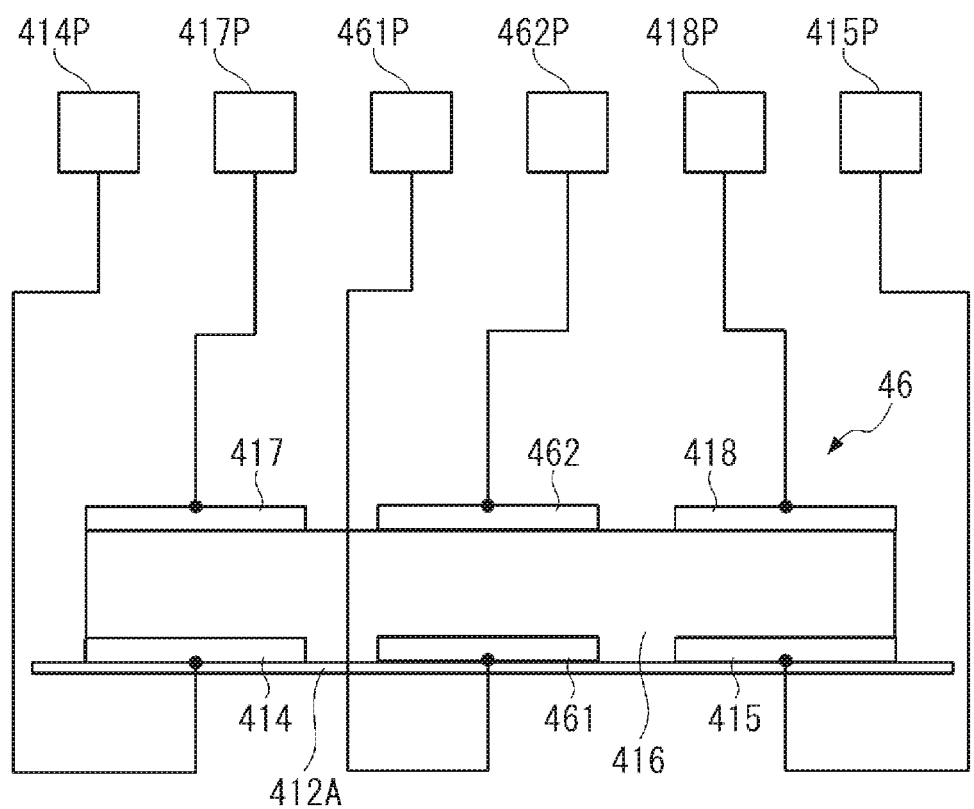
FIG. 12 is a diagram schematically showing a relationship between the ultrasonic transducer and an electrode pad in the second embodiment.

FIG. 10 is a plan view schematically showing an ultrasonic transducer 46 when viewed from the side of the acoustic lens 44. FIG. 11 is a sectional view schematically showing a cross section of the ultrasonic transducer 46. In addition, FIG. 12 is a diagram schematically showing a relationship between the electrodes included in the ultrasonic transducer 46 and electrode pads corresponding to the electrodes.

The ultrasonic transducer 46 is configured to include the flexible film 412A and a piezoelectric element 413A which is provided on the flexible film 412A. Also in the embodiment, the ultrasonic transducer group constituting one transmitting/receiving channel is configured to have a plurality of ultrasonic transducers 46 disposed in the Y direction. In addition, the plurality of ultrasonic transducer groups are disposed in the X direction and constitute the ultrasonic array AL.

In the embodiment, as shown in FIGS. 10 and 11, the piezoelectric element 413A is configured to include a third lower electrode 461 and a third upper electrode 462, in addition to the first lower electrode 414, the second lower electrode 415, the piezoelectric film 416, the first upper electrode 417, and the second upper electrode 418. The electrodes 414, 415, 417, 418, 461, and 462 are in contact with the piezoelectric film 416 and are separated from each other.

As shown in FIG. 10, the third lower electrode 461 corresponds to a fifth electrode and is provided at a position at which the third lower electrode overlaps the piezoelectric film 416 on the surface of the flexible film 412A on the +Z side in the plan view when viewed in the Z direction. In addition, as shown in FIG. 10, the third lower electrode 461 has a substantially rectangular planar shape and is disposed at a position at which the third lower electrode overlaps the virtual line L parallel to the Y direction through the central position of the piezoelectric film 416. In addition, as shown in FIG. 11, an end surface 461B of the third lower electrode 461 on the −X side is separated from the end surface 414C of the first lower electrode 414 on the +X side by a gap G3 having a predetermined dimension in the X direction. In addition, an end surface 461C of the third lower electrode 461 on the +X side is separated from the end surface 415C of the second lower electrode 415 by the gap G3 having the predetermined dimension in the X direction.

In addition, similar to the first lower electrode 414 or the like, the third lower electrode 461 is connected to a third lower electrode 461 of an adjacent ultrasonic transducer 46 in the Y direction, with a third lower electrode line 461A. Although not shown, the third lower electrodes 461 of the ultrasonic transducers 46 disposed at both ends of the ultrasonic transducer group in the Y direction are connected to third lower electrode pads 461P (refer to FIG. 12) formed in the terminal region Ar2, with third lower electrode leading lines (not shown).

As shown in FIG. 10, the third upper electrode 462 corresponds to a sixth electrode and is provided at a position at which the third upper electrode overlaps the third lower electrode 461 on the surface of the piezoelectric film 416 on the +Z side in the plan view when viewed in the Z direction. In other words, the third lower electrode 461 and the third upper electrode 462 are separated via the piezoelectric film 416 (interposed therebetween) and overlap each other in the plan view. An end surface 462B of the third upper electrode 462 on the −X side is separated from the end surface 417C of the first upper electrode 417 on the +X side by the gap G3 having the predetermined dimension in the X direction. In addition, an end surface 462C of the third upper electrode 462 on the +X side is separated from the end surface 418C of the second upper electrode 418 on the −X side by the gap G3 having the predetermined dimension in the X direction.

In addition, similar to the third lower electrode 461, the third upper electrode 462 is connected to a third upper electrode 462 of an adjacent ultrasonic transducer 46 in the Y direction, with a third upper electrode line 462A. Although not shown, the third upper electrodes 462 of the ultrasonic transducers 46 disposed at both ends of the ultrasonic transducer group in the Y direction are connected to third upper electrode pads 462P (refer to FIG. 12) formed in the terminal region Ar2, with third lower electrode leading lines (not shown).

The ultrasonic transducer 46 configured as described above is connected to the switch circuit 231 of the circuit substrate 23 via the electrode pads 414P, 415P, 417P, 418P, 461P, and 462P shown in FIG. 12. Also in the embodiment, the switch circuit 231 switches the connection between the electrode pads 414P, 415P, 417P, and 418P, between the first connection state that is selected when the ultrasonic wave is transmitted and the second connection state that is selected when the ultrasonic wave is received.

Specifically, in the first connection state selected when the ultrasonic wave is transmitted, the switch circuit 231 is connected to the first lower electrode pad 414P, the second lower electrode pad 415P, and the third lower electrode pad 461P. In this manner, the lower electrodes 414, 415, and 461 are short-circuited. Here, in the embodiment, the third lower electrode 461 is wired to function as the SIG electrode regardless of the connection state. In other words, in the first connection state, the electrodes 414, 415, and 461 which are short-circuited from each other function as the SIG electrodes.

In addition, in the first connection state, the switch circuit 231 is connected to the first upper electrode pad 417P, the second upper electrode pad 418P, and the third upper electrode pad 462P. In this manner, the upper electrodes 417, 418, and 462 are short-circuited. Here, in the embodiment, the first upper electrode 417 and the second upper electrode 418 are wired to function as the COM electrode regardless of the connection state. In other words, the lower electrodes 417, 418, and 462 which are short-circuited from each other function as the COM electrodes.

In the first connection state, the voltages are applied between the first lower electrode 414 and the first upper electrode 417, between the second lower electrode 415 and the second upper electrode 418, and between the third lower electrode 461 and the third upper electrode 462. In this manner, the piezoelectric element 413A is driven, and the ultrasonic wave is detected.

On the other hand, in the second connection state selected when the ultrasonic wave is received, the switch circuit 231 is connected to the first lower electrode pad 414P, the second lower electrode pad 415P, the first upper electrode pad 417P, and the second upper electrode pad 418P. In other words, in the second connection state, the first lower electrode 414, the second lower electrode 415, the first upper electrode 417, and the second upper electrode 418 are short-circuited from each other and function as the COM electrodes.

In addition, in the second connection state, the switch circuit 231 is connected to the third lower electrode pad 461P and the third upper electrode pad 462P. In other words, in the second connection state, the third lower electrode 461 and the third upper electrode 462 are short-circuited from each other and function as the SIG electrodes.

In the second connection state, the signal in response to the potential difference between the first lower electrode 414 (the second lower electrode 415) and the third lower electrode 461 (that is, the potential difference between the first upper electrode 417 (the second upper electrode 418) and the third upper electrode 462) is output to the receiving circuit 234.

In the embodiment, in the second connection state, the switch circuit 231 is configured such that the first lower electrode 414, the second lower electrode 415, the first upper electrode 417, and the second upper electrode 418 function as the COM electrode, and the third lower electrode 461 and the third upper electrode 462 function as the SIG electrode; however, the configuration is not limited thereto. For example, the switch circuit 231 may be configured such that the first lower electrode 414, the second lower electrode 415, the first upper electrode 417, and the second upper electrode 418 function as the SIG electrode, and the third lower electrode 461 and the third upper electrode 462 function as the COM electrode.

Operational Effect of Second Embodiment

In the embodiment, the piezoelectric element 413A includes the third lower electrode 461 and the third upper electrode 462 which overlap each other in the plan view, the third lower electrode 461 is positioned between the first lower electrode 414 and the second lower electrode 415, and the third upper electrode 462 is positioned between the first upper electrode 417 and the second upper electrode 418.

In addition, when the ultrasonic wave is received, the switch circuit 231 switches the connection state to the second connection state in which the first lower electrode 414, the first upper electrode 417, the second lower electrode 415, and the second upper electrode 418 are short-circuited, and the third lower electrode 461 and the third upper electrode 462 are also short-circuited. In this manner, a capacitor formed by the first lower electrode 414 and the third lower electrode 461, a capacitor formed by the second lower electrode 415 and the third lower electrode 461, a capacitor formed by the first upper electrode 417 and the third upper electrode 462, and a capacitor formed by the second upper electrode 418 and the third upper electrode 462 are connected in parallel. Hence, it is possible to more increase the stray capacitance of the ultrasonic transducer 46, and it is possible to more easily perform the impedance matching with the external circuit, compared to a configuration in which the capacitors are not connected in parallel.

In addition, when the ultrasonic wave is transmitted, the switch circuit 231 switches the connection state to the second connection state in which the lower electrodes 414, 415, and 461 are short-circuited, and the upper electrodes 417, 418, and 462 are short-circuited. Here, the third lower electrode 461 and the third upper electrode 462 are disposed at the central portion of the piezoelectric film 416 when viewed in the Z direction. Hence, when the ultrasonic wave is transmitted, it is possible to drive the central portion of the piezoelectric element 413A, and it is possible to improve the transmission output of the ultrasonic wave.

Modification Example

The present invention is not limited to the embodiments described above, and the present invention also includes a configuration obtained through modification, improvement, and an appropriate combination of the embodiments in a range in which it is possible to achieve the object of the present invention.

In the second embodiment, a configuration in which, in a case where the ultrasonic wave is transmitted by using the ultrasonic transducer 46, the switch circuit 231 switches the connection state to the first connection state and, then, applies the voltages between the first lower electrode 414 and the first upper electrode 417, between the second lower electrode 415 and the second upper electrode 418, and between the third lower electrode 461 and the third upper electrode 462 is exemplified. However, the configuration is not limited thereto. For example, a configuration in which, in the case where the ultrasonic wave is transmitted, the voltage is applied only between the third lower electrode 461 and the third upper electrode 462 may be employed.

In this case, a configuration in which the switch circuit 231 switches the connection state to the first connection state in which the third lower electrode 461 and the third upper electrode 462 are individually connected to the selection circuit 232 when the ultrasonic wave is transmitted, and the switch circuit switches the connection state to the second connection state in which the third lower electrode 461 and the third upper electrode 462 are short-circuited when the ultrasonic wave is received.

In this case, it is possible to use the first lower electrode 414, the first upper electrode 417, the second lower electrode 415, and the second upper electrode 418 as the COM electrodes. In other words, it is possible to employ a configuration in which the switch circuit 231 causes the first lower electrode 414, the first upper electrode 417, the second lower electrode 415, and the second upper electrode 418 to be short-circuited at the time of both of the transmission and the reception. In this manner, it is possible to simplify the driving process of the ultrasonic transducer 46, and it is possible to increase the processing load.

When the ultrasonic wave is transmitted, the switch circuit 231 may be configured to be capable of selecting the configuration of the modification example in which the voltage is applied only between the third lower electrode 461 and the third upper electrode 462 and the configuration of the second embodiment in which the voltages are applied between all of the electrodes.

In the second embodiment, the configuration in which one electrode is provided both between the first lower electrode 414 and the second lower electrode 415 and between the first upper electrode 417 and the second upper electrode 418 is exemplified; however, the configuration is not limited thereto, and a configuration in which two or more electrodes are disposed therebetween may be employed.

Figure 13:
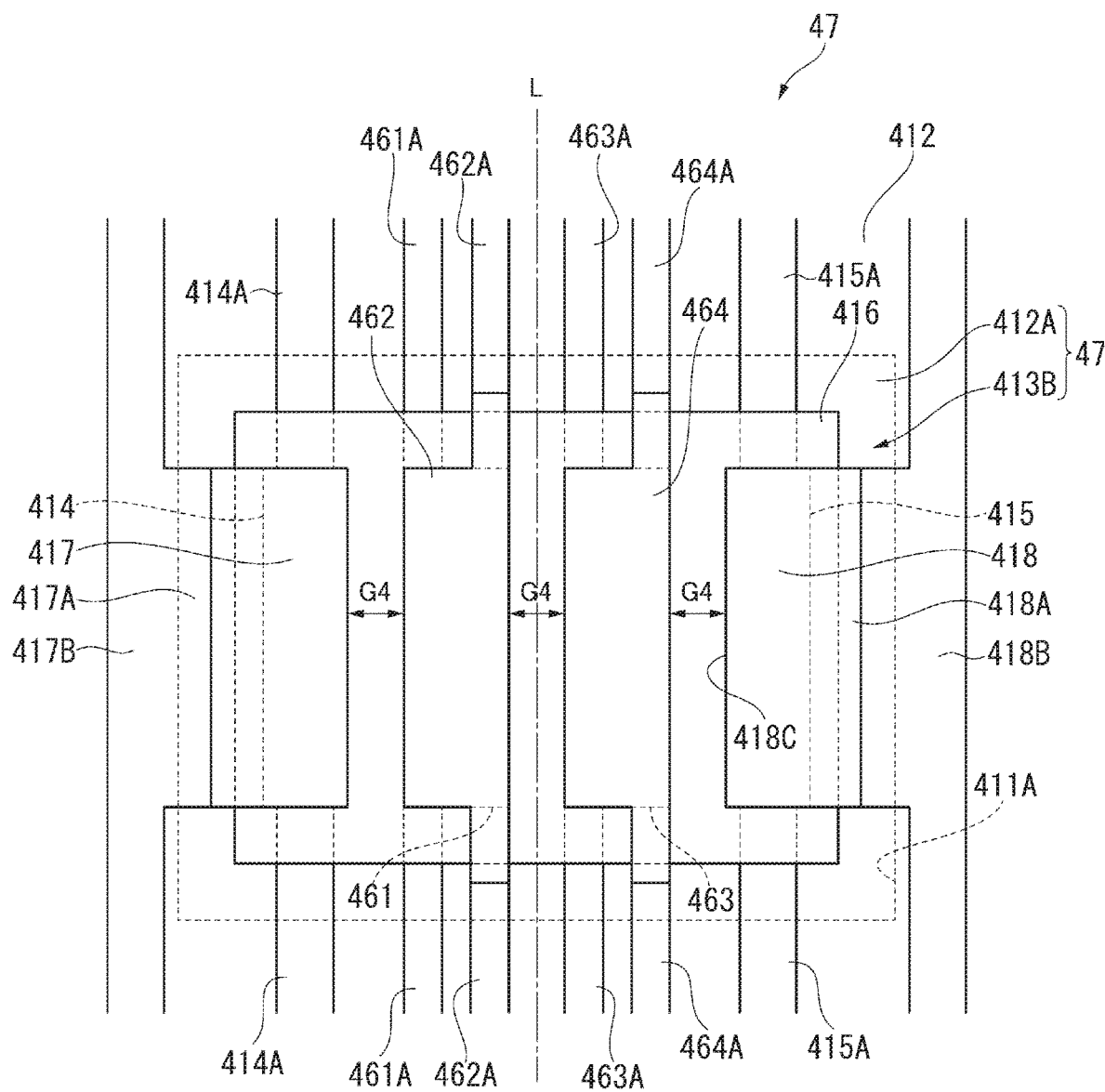
FIG. 13 is a plan view showing a schematic configuration of a modification example of an ultrasonic transducer.

FIG. 13 is a plan view showing an ultrasonic transducer 47 according to a modification example.

In the example shown in FIG. 13, the ultrasonic transducer 47 has a configuration in which a piezoelectric element 413B is disposed on the flexible film 412A. In the piezoelectric element 413B, the third lower electrode 461 and a fourth lower electrode 463 are disposed in this order from the −X side between the first lower electrode 414 and the second lower electrode 415.

The lower electrodes 414, 415, 461, and 463 are disposed to be substantially mirror-symmetric to the virtual line L in the plan view. In addition, the lower electrodes 414, 415, 461, and 463 are separated from each other via a gap G4 having a predetermined dimension in the X direction.

The fourth lower electrode 463 has a substantially similar configuration to that of the third lower electrode 461 and is connected to a fourth lower electrode 463 of an adjacent ultrasonic transducer 47 in the Y direction, with a fourth lower electrode line 463A. In addition, the ultrasonic transducer group is configured of a plurality of ultrasonic transducers 47 disposed in the Y direction, and the fourth lower electrode 463 is connected to a fourth lower electrode pad (not shown) in the ultrasonic transducers 47 disposed at both ends of the ultrasonic transducer group in the Y direction.

In addition, the third upper electrode 462 and a fourth upper electrode 464 are disposed in this order from the −X side between the first upper electrode 417 and the second upper electrode 418. The upper electrodes 417, 418, 462, and 464 are disposed to be substantially mirror-symmetric to the virtual line L in the plan view. In addition, the upper electrodes 417, 418, 462, and 464 are separated from each other via the gap G4 having the predetermined dimension in the X direction.

The fourth upper electrode 464 has a substantially similar configuration to that of the third upper electrode 462 and is connected to a fourth upper electrode 464 of an adjacent ultrasonic transducer 47 in the Y direction, with a fourth upper electrode line 464A. In addition, the fourth upper electrode 464 is connected to a fourth upper electrode pad (not shown) in the ultrasonic transducers 47 disposed at both ends of the ultrasonic transducer group in the Y direction.

For example, in a case where the ultrasonic wave is transmitted by using the ultrasonic transducer 47, the switch circuit 231 is configured to switch the connection state to the first connection state in which the lower electrodes 414, 415, 461, and 463 are short-circuited, and the upper electrodes 417, 418, 462, and 464 are short-circuited. In the first connection state, the lower electrodes 414, 415, 461, and 463 function as the SIG electrodes, the upper electrodes 417, 418, 462, and 464 function as the COM electrodes, voltages are applied between the electrodes disposed to overlap each other in the Z direction, and the thereby the ultrasonic wave is transmitted from the ultrasonic transducer 47.

In addition, in a case where the ultrasonic wave is transmitted by using the ultrasonic transducer 47, the switch circuit 231 is configured to switch the connection state to the second connection state in which the first lower electrode 414, the first upper electrode 417, the fourth lower electrode 463, and the fourth upper electrode 464 are short-circuited, and the second lower electrode 415, the second upper electrode 418, the third lower electrode 461, and the third upper electrode 462 are short-circuited. In the second connection state, the first lower electrode 414, the first upper electrode 417, the fourth lower electrode 463, and the fourth upper electrode 464 function as the SIG electrodes, the second lower electrode 415, the first upper electrode 418, and the third lower electrode 461, and the third upper electrode 462 function as the COM electrodes, and the electric signal in response to the strain of the piezoelectric film 416 is output from the ultrasonic transducer 47.

In the ultrasonic transducer 47 configured as described above, it is possible to reliably increase the capacitance of the ultrasonic transducer 47 in the second connection state.

In addition, similarly to the first embodiment, the third lower electrode 461 and the fourth lower electrode 463 which constitute the capacitor in the second connection state are separated from each other with the central portion of the piezoelectric film 416 therebetween in the X direction. In addition, the same is true of the third upper electrode 462 and the fourth upper electrode 464. Hence, when the ultrasonic wave is received, it is possible to increase the potential difference between the third lower electrode 461 and the fourth lower electrode 463 and between the third upper electrode 462 and the fourth upper electrode 464 which constitute capacitors, and it is possible to improve the receiving sensitivity of the ultrasonic wave.

In the embodiments, a configuration in which the lower electrode is provided on a surface (surface on the −Z side) of the piezoelectric film 416 on the side of the flexible film 412A, and the upper electrode is provided on a surface (surface on the +Z side) of the piezoelectric film 416 on an opposite side to the flexible film 412A is exemplified; however, the configuration is not limited thereto. For example, the upper electrodes may not be provided on the surface of the flexible film 412A on the +Z side but may be provided on the surface on the −Z side. In such a configuration, a part of the piezoelectric film 416 covers the upper electrodes, and thereby it is possible to suppress the degradation of the upper electrodes. In addition, similarly, the lower electrodes may not be provided on the surface of the piezoelectric film 416 on the −Z side but may be provided on the surface on the +Z side, that is, may be disposed inside the piezoelectric film 416.

In addition, an electrode may be disposed between the first lower electrode 414 and the first upper electrode 417 which are an electrode set and overlap in the Z direction, or an electrode may be disposed between the second lower electrode 415 and the second upper electrode 418. In addition, in the second embodiment, an electrode may be further disposed between the third lower electrode 461 and the third upper electrode 462. In addition, in the embodiments, the configuration in which a plurality of electrode sets configured of the electrodes, which overlap each other in the Z direction, are disposed in the X direction, and each electrode is configured of the same number of electrodes is exemplified; however, the number of electrode sets may be different.

In the embodiment, a configuration in which the lower electrode is disposed in the same surface orthogonal to the Z direction; however, the configuration is not limited thereto, and the positions of the lower electrodes in the Z direction may be different. In addition, the same is true of the upper electrodes.

In the embodiments, the ultrasonic apparatus 1 has a configuration in which the first polarization process is performed after the connection state is switched to the first connection state and before the ultrasonic wave is transmitted, and the second polarization process is performed after the connection state is switched to the second connection state and before the ultrasonic wave is transmitted, is exemplified; however, the configuration is not limited thereto. For example, it may not be absolutely necessary to execute the first polarization process whenever the ultrasonic wave is transmitted, and the first polarization process may be executed only at a predetermined timing (for example, when a predetermined time has elapsed). In addition, similar to the second polarization process, it may not be absolutely necessary to execute the second polarization process whenever the ultrasonic wave is received, and the second polarization process may be executed only at a predetermined timing.

In addition, only the first polarization process may be executed, or only the second polarization process may be executed.

In the embodiment, a configuration, in which the switch circuit 231 that switches the connection state of the electrodes of the ultrasonic transducer between the first connection state and the second connection state is provided, is exemplified, the configuration is not limited thereto, and a configuration, in which the switch circuit 231 is not provided, may be employed, for example. For example, In the ultrasonic transducer 45 of the first embodiment, when the ultrasonic wave is transmitted, the voltage is applied between the electrode pads (for example, between the first lower electrode pad 414P and the first upper electrode pad 417P) such that the voltage is applied between the pair of electrodes which overlap each other in the Z direction, and thereby it is possible to improve the transmission output of the ultrasonic wave. In addition, when the ultrasonic wave is received, both of the potential difference generated between the lower electrodes 414 and 415 and the potential difference generated between the upper electrodes 417 and 418 are detected. In this manner, it is possible to detect the ultrasonic wave, and it is possible to improve the receiving sensitivity as described above.

In the embodiments, a configuration in which the acoustic matching layer 43 and the acoustic lens 44 are provided on the opposite side to the substrate main body 411 of vibration film 412 (flexible film 412A) is exemplified; however, the configuration is not limited thereto.

For example, a configuration in which the acoustic matching layer 43 and the acoustic lens 44 are provided on the side of the substrate main body 411 of the vibration film 412 (the flexible film 412A), and the opening 411A is filled with the acoustic matching layer 43 may be employed. In this case, there is employed a configuration in which the sealing plate 42 is provided on the opposite side to the substrate main body 411 of the vibration film 412, and a recessed groove is positioned to be opposite to the opening 411A in the plan view. In such a configuration, the piezoelectric element or the wirings of the ultrasonic transducer are not exposed on the side of the acoustic matching layer 43, it is possible to increase the waterproof property in the ultrasonic device 22.

In the embodiments described above, the ultrasonic apparatus that has the organ in the living body as the measurement target is described; however, the embodiment is not limited thereto. For example, the present invention can be applied to a measuring instrument that detects a defect and inspects for aging of a structure, with various type of structures as the measurement target. In addition, the present invention can also be applied to a measuring instrument that detects a defect of a measurement target, with a semiconductor package, a wafer, or the like as the measurement target.

In addition, the specific structures of the embodiments of the present invention may be configured by appropriately combining the embodiments and modification examples and may be appropriately modified to have another structure in a range in which it is possible to achieve the object of the invention.

The invention claimed is:

1. An ultrasonic module comprising:
an ultrasonic transducer that includes a flexible film and a piezoelectric element which is provided on the flexible film; and
a circuit substrate that is connected to the piezoelectric element, the circuit substrate including a switch, the switch switching between a first connection state and a second connection state,
wherein the piezoelectric element includes a piezoelectric body and a first electrode, a second electrode, a third electrode, and a fourth electrode that are in contact with the piezoelectric body,
the first electrode and the second electrode sandwich the piezoelectric body, and the first electrode and the second electrode overlap each other in a plan view when viewed from a top of the piezoelectric body along a first direction,
the third electrode and the fourth electrode sandwich the piezoelectric body therebetween, and the third electrode and the fourth electrode overlap each other in the plan view,
the first electrode and the third electrode are separated from each other in the plan view, and the second electrode and the fourth electrode are separated from each other in the plan view,
wherein, when the switch is in the first connection state, the first electrode and the third electrode are short-circuited, and the second electrode and the fourth electrode are short-circuited, and
when the switch is in the second connection state, the first electrode and the second electrode are short-circuited, and the third electrode and the fourth electrode are short-circuited.

2. The ultrasonic module according to claim 1, wherein a distance between the first electrode and the fourth electrode is longer than a distance between the first electrode and the third electrode when viewed in a sectional view in a direction perpendicular to the plan view.

3. The ultrasonic module according to claim 1, wherein the first electrode and the third electrode are located at one side of the piezoelectric body in the first direction, and the second electrode and the fourth electrode are located at an opposing side to the one side of the piezoelectric body in the first direction, and the first electrode has a first end surface which faces the third electrode in a second direction perpendicular to the first direction, and the second electrode has a second end surface which faces the fourth electrode in the second direction, and the first end surface of the first electrode overlaps with the second end surface of the second electrode in the plan view.

4. An ultrasonic apparatus comprising:
an ultrasonic transducer that includes a flexible film and a piezoelectric element which is provided on the flexible film:
a controller configured to control the ultrasonic transducer; and
a switch switching between a first connection state and a second connection state,
wherein the piezoelectric element includes a piezoelectric body and a first electrode, a second electrode, a third electrode, and a fourth electrode that are in contact with the piezoelectric body, the first electrode and the second electrode sandwich the piezoelectric body, and the first electrode and the second electrode overlap each other in a plan view when viewed from a top of the piezoelectric body, the third electrode and the fourth electrode sandwich the piezoelectric body, and the third electrode and the fourth electrode overlap each other in the plan view, the first electrode and the third electrode are separated from each other in the plan view, and the second electrode and the fourth electrode are separated from each other in the plan view, wherein, when the switch is in the first connection state, the first electrode and the third electrode are short-circuited, and the second electrode and the fourth electrode are short-circuited, and when the switch is in the second connection state, the first electrode and the second electrode are short-circuited, and the third electrode and the fourth electrode are short-circuited.

5. The ultrasonic apparatus according to claim 4, wherein the controller is configured to control the switch to be in the first connection state when the ultrasonic transducer transmits an ultrasonic wave, and the controller is configured to control the switch to be in the second connection state when the ultrasonic transducer receives an ultrasonic wave.

6. The ultrasonic apparatus according to claim 4, wherein the controller includes a polarization control unit, and the polarization control unit is configured to execute a first polarization process in which a first polarization voltage is applied between the first electrode and the second electrode and between the third electrode and the fourth electrode.

7. The ultrasonic apparatus according to claim 4, wherein the controller includes a polarization control unit, and the polarization control unit is configured to execute a second polarization process in which a second polarization voltage is applied between the first electrode and the third electrode and between the second electrode and the fourth electrode.

* * * * *